US012756762B2

(12) United States Patent
Grosskopf et al.

(10) Patent No.: US 12,756,762 B2
(45) Date of Patent: Oct. 6, 2026

(54) SYSTEM AND METHOD FOR DATA INTERROGATION AND/OR REMOTE PROGRAMMING OF A MEDICAL DEVICE WITH REDUCED LATENCY

(71) Applicant: BIOTRONIK SE & Co. KG, Berlin (DE)

(72) Inventors: Rainer Joerg Grosskopf, Portland, OR (US); James Horton, Portland, OR (US); Thorsten Wenzlaff, Berlin (DE); Dirk Kleeblatt, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 312 days.

(21) Appl. No.: 18/284,799

(22) PCT Filed: Mar. 29, 2022

(86) PCT No.: PCT/EP2022/058222
§ 371 (c)(1),
(2) Date: Sep. 28, 2023

(87) PCT Pub. No.: WO2022/207614
PCT Pub. Date: Oct. 6, 2022

(65) Prior Publication Data

US 2024/0371513 A1 Nov. 7, 2024

Related U.S. Application Data

(60) Provisional application No. 63/167,708, filed on Mar. 30, 2021.

(51) Int. Cl.
*H04L 67/142* (2022.01)
*G16H 40/40* (2018.01)
(Continued)

(52) U.S. Cl.
CPC ........... *H04L 67/142* (2013.01); *G16H 40/40* (2018.01); *G16H 40/67* (2018.01); *H04L 67/12* (2013.01);
(Continued)

(58) Field of Classification Search
CPC ........ G16H 40/20; G16H 40/40; G16H 40/67; H04L 67/12; H04L 67/67; H04L 67/142; H04L 67/148; H04W 76/11; H04W 76/25
See application file for complete search history.

(56) References Cited

U.S. PATENT DOCUMENTS 7,369,897 B2 5/2008 Boveja et al.
8,868,201 B2 * 10/2014 Roberts ................ H04L 63/068 607/60
(Continued)

FOREIGN PATENT DOCUMENTS

WO WO 2020/083585 A1 4/2020

OTHER PUBLICATIONS

Stevens et al, "A Cyber-Physical System for Near Real-Time Monitoring of At-Home Orthopedic Rehabilitation and Mobile-Based Provider-Patient Communications to Improve Adherence: Development and Formative Evaluation", May 11, 2020, JMIR Hum Factors 2020, https://humanfactors.jmir.org/2020/2/e16605 (Year: 2020).*
(Continued)

*Primary Examiner* — Akwasi M Sarpong
*Assistant Examiner* — Gabrielle N Dai
(74) *Attorney, Agent, or Firm* — EBT Gibbons LLP

(57) ABSTRACT

A method is used for establishing a communication connection between at least one health care professional remote device and at least one medical device. The method includes the steps of:

establishing a first communication connection between the CP with a remote monitoring server, (Continued)

establishing a second communication connection between the RMS and a patient remote device, and
establishing a third communication connection between the PR and the medical device.
The CP is configured to optimize an internal device process such that the first communication connection can be maintained as continuous communication connection, and/or the PR is configured to optimize an internal device process such that the second and/or third communication connection can be maintained as continuous communication connection. A remote programming session and/or interrogation session of the medical device is initiated if the communication connection between the CP and the medical device is successfully established.

20 Claims, 20 Drawing Sheets

(51) Int. Cl.

| | |
|---|---|
| ***G16H 40/67*** | (2018.01) |
| ***H04L 67/12*** | (2022.01) |
| ***H04L 67/148*** | (2022.01) |
| ***H04W 76/11*** | (2018.01) |
| ***H04W 76/25*** | (2018.01) |

(52) U.S. Cl.
CPC .......... *H04L 67/148* (2013.01); *H04W 76/11* (2018.02); *H04W 76/25* (2018.02)

(56) References Cited

U.S. PATENT DOCUMENTS

| | | | | |
|---|---|---|---|---|
| 8,970,392 | B2 * | 3/2015 | LaLonde | G08C 17/02 340/870.01 |
| 9,807,195 | B2 * | 10/2017 | Mark | G06F 3/0484 |
| 10,576,290 | B2 * | 3/2020 | Schilling | A61N 1/37254 |
| 10,675,475 | B2 * | 6/2020 | Rao | G16H 40/67 |
| 11,818,222 | B2 * | 11/2023 | Grosskopf | G16H 40/20 |
| 2009/0262688 | A1 | 10/2009 | Tsai et al. | |
| 2014/0062718 | A1 | 3/2014 | LaLonde et al. | |

OTHER PUBLICATIONS

K151901, Department of Health & Human Services, Letter regarding Trade/Device Name: AirView, dated Nov. 5, 2015; 9 pages.
K161686, Department of Health & Human Services, Letter regarding Trade/Device Name: F&P InfoSmart, dated Jan. 24, 2017; 8 pages.
K181053, FDA U.S. Food & Drug Administration, Letter regarding Trade/Device Name: Care Orchestrator, dated Jan. 4, 2019, 7 pages.
International Search Report and Written Opinion dated Jul. 22, 2022, for International Application No. PCT/EP2022/058222, 16 pages.
Anonymous: "Data warehouse—Wikipedia, the free encyclopedia", dated Jan. 12, 2015, retrieved from the Internet <https://en.wikipedia.org/w/index.php?title=Datawarehouse&oldid=642174526> retrieved on Mar. 18, 2016.

* cited by examiner

SYSTEM AND METHOD FOR DATA INTERROGATION AND/OR REMOTE PROGRAMMING OF A MEDICAL DEVICE WITH REDUCED LATENCY

This invention disclosure describes a system and method to provide remote programming to medical devices and/or interrogation of data from medical devices.

Medical devices such as implants as known in the art can be coupled with various external devices to exchange data. For example, an implantable medical device can be coupled with a programmer that allows a health care professional (HCP), such as a clinician, to adjust the implantable medical device's settings. For coupling, a magnetic switch can, for example, be used, which is placed over the implantable medical device. The magnetic switch has a permanent magnet whose magnetic field is detected by the implantable medical device and puts it into a coupling state in which the implantable medical device is coupled to the programmer.

In addition, in a wireless monitoring system, a patient device is known to connect wirelessly to a medical device when located near the medical device. Such patient devices are used, for example, to download patient data at regular intervals (e.g. daily) from the implantable medical device and forward it to a service centre. At the service centre, the data are pre-processed and, if necessary, transferred to a user, e.g. an HCP.

A patient device may, for example, be equipped with a wake-up function to switch an associated implantable medical device from a resting state to an active state in order to establish a communication link with the implantable medical device. The patient device for example emits a wake-up signal in a radio frequency (RF) range, which is received by the implantable medical device, whereupon it is activated for data communication with the patient device.

A potential disadvantage of a general wake-up functionality to wake up an implantable medical device is that unwanted access to the implantable medical device can potentially be gained by third-party devices that implement the patient device's communication scheme and methodology. Especially, in the field of implantable medical devices with vital therapy functions such as pacemakers and implantable cardioverter defibrillators, demands on cybersecurity are generally high.

In addition, systems exist providing the possibility for a patient to initiate a recording of data by the implantable medical device. If, for example, a pacemaker patient does not feel well, e.g., if the patient feels dizzy or experiences a tachycardia, the patient can trigger the recording of an ECG by the implantable medical device, e.g. by actuating a remote control. The data recorded in this way is transferred directly to an HCP or to a service centre the next time data is retrieved from the implantable medical device, for example during an examination at the clinician or via an automatic query of the patient device.

Generally, processes to access real-time status data from an implantable medical device, such as an implantable pulse generator (IPG), are presently limited to interrogated data gathered during an in-clinic follow-up or, in limited examples, a report triggered by the patient. These processes lack clinician control. Although some implantable medical devices have means for triggering an interrogation when the patient is remote from a clinician, the patient generally is involved as an actor able to trigger the remote interrogation, the clinician currently having limited ability to trigger the remote interrogation by himself.

In a typical workflow, as provided by some products currently available, a patient, who feels symptomatic, may wish to send a report to a clinic, or the clinic may request that the patient generate a report. In either case, the patient follows the process to initiate the patient device to trigger the interrogation. This requires either that the patient places an interrogation wand over the implanted medical device, or if available, the patient device can connect to the implanted medical device via wireless means. The implanted medical device processes the interrogation and transmits data to the patient device. The patient then triggers the patient device to transmit an interrogation message, for example, to a service centre, or if available, the patient device initiates the transmission to the service centre automatically.

Thus, such solutions are patient-triggered in the sense that clinicians must rely on the patient to initiate the data capture and possibly the data transmission as well, and are therefore not in control of how or when the data is captured. Further, as the clinic cannot control receipt of the information transmitted from the implant, an HCP is not necessarily able to respond to the receipt of the data at the time it is received. This leads to a non-optimal workflow regarding the clinic review of the data. Because the transmission of data triggered by the patient and the receipt and review by the clinic are disconnected from one another, potentially a liability situation may be caused, if the clinic does not respond in a timely fashion.

Document U.S. Pat. No. 7,369,897 discloses a method and system of remotely controlling an implanted stimulator for providing electrical pulses to nerve tissue, comprising an implantable stimulator, an interface unit, and a mobile device such as a modified PDA or cell phone. Document WO 2020/083585 A1 discloses a method for initiating a data transfer from an implantable medical device. This document provides a means to remotely interrogate an implantable medical device via a trigger initiated by a clinician. Having the process triggered by the clinician rather than the patient allows the clinician to be in control of the process.

State-of-the-art implanted pacemakers, cardiac monitors, neuro stimulators and similar implantable medical devices communicate with an HCP user interface during a face-to-face visit with an HCP. During the face-to-face visit the programmer provides a real-time view of diagnostic and technical data.

Typically, these implanted devices can also transmit diagnostic and technical data periodically to a server. HCPs access this data through a secure website. This enables them to remotely track their patients. However, the data transmission delays in existing remote monitoring designs are too limiting for HCPs to provide more complex care to their patients. For example, neuro stimulation systems require interactive feedback from patient to clinician in order to adjust the stimulation therapy effectively. Providing such interactions remotely is not possible with today's systems. In cardiac rhythm management, it is desirable to be able to view an IEGM and device status in real-time when a patient contacts the clinic and reports the onset of an event. Viewing the intracardiac electrogram and system data in real-time allows the HCP to accurately triage the patient and determine required next steps. Even though cardiac rhythm management devices are typically capable of detecting and recording events, it should not be assumed that the device has always been correctly programmed to detect the event.

As these implanted devices typically transmit based only upon an internal trigger (e.g. event detection, scheduled update transmission), the data transmitted from them are typically not up to date at the time of an in-office check.

Accordingly, the device is typically interrogated at the start of any office visit, with resulting clinical labor cost and time delay. This function could be performed in advance of the patient visit if interrogation is available to the clinic remotely.

Accordingly, there is a need to provide data interrogation or device programming remotely and in real-time in order to avoid patient interaction and to reduce data transmission latency, increase data transmission rate, reduce impact to the medical device size and battery longevity. Further, clinic workflows need to be optimized in order to reduce costs.

The above object is solved by a method having the features of claim 1 and a system with the features defined in claim 12.

In particular, a method for establishing a communication connection between at least one health care professional (HCP) remote device (CP) and at least one medical device is proposed. The method comprises the steps of:

- establishing a first communication connection between the CP with a remote monitoring server (RMS),
- establishing a second communication connection between the RMS and a patient remote device (PR),
- establishing a third communication connection between the PR and the medical device.

Moreover, the CP is configured to optimize an internal device process such that the first communication connection can be maintained as continuous communication connection. Alternatively or in addition, the PR is configured to optimize an internal device process such that the second and/or third communication connection can be maintained as a continuous communication connection. If the communication connection between the CP and the medical device is successfully established, a remote programming session and/or interrogation session of the medical device is initiated.

According to an embodiment of the present invention, the CP and/or the PR is configured to optimize an internal device process such that the computational resources are prioritized to establish and maintain the remote programming session and/or interrogation session of the medical device. The optimization of the internal device process can contain at least one of the following measures:

- Reduction of the number of internal device software applications and/or reducing an internal device access to software applications to those required for maintaining the first communication connection as continuous communication connection, and/or
- Reduction of the internal device data traffic to that required for maintaining the first communication connection as continuous communication connection, and/or Reduction of the internal device communication applications to that required for maintaining the first communication connection as continuous communication connection.

According to exemplary embodiments of the present invention, necessary software applications may be those for connection and communication with the RMS, software applications associated with the operating system and/or the Mobile Device Management (MDM) provider, etc.

For instance, for reduction of software applications or for a reduction of an access to software applications:

- No internet browser is installed in the PR and/or CP, or a browser is installed, but the browser selection and the list of acceptable URLs is controlled by the MDM system, and/or
- The internet resources of the PR and/or the CP may be whitelisted to only those resources that are needed for said purpose, and/or
- The access of the PR and/or the CP to an app store (e.g. Microsoft Store, Google Play Store) may be limited to a reduced set of apps, e.g. privately published apps, and/or
- Messaging and phone apps of the PR and/or the CP are disabled.

Preferably, according to an embodiment of the invention, for establishing the second communication connection between the RMS and the PR, the RMS initiates delivery of a notification from an external messaging provider to the PR. In an example, the external messaging provider is a push notification messaging provider. For instance, the PR, upon receiving the notification, starts polling information from the RMS at a predetermined rate. For instance, the polling rate is less than or equal to 1063.75 kilobit per second (KBPS).

If the PR would be configured to continuously poll the RMS for changes, that would result in unnecessary computational overhead on both the PR and RMS, i.e., in terms of data usage from the PR perspective and request processing from the RMS perspective. Instead, according to an embodiment of the invention, in case a communication connection should be established between the RMS and the PR, the RMS will communicate with an external push notification system, to initiate a notification to the PR. Conceptually, at the beginning of a remote programming session of the implantable device, the PR receives a push notification. This notification serves as a trigger to the PR to poll the RMS at a predetermined rate. The predetermined rate may be higher than the rate the PR normally uses to poll the RMS if no remote programming session is requested.

Preferably, according to an embodiment of the present invention, the remote programming session and/or interrogation session is associated with at least one first session identifier. As soon as the communication connection between the CP and the implantable device is established, i.e. first, second and third communication connections are successfully established, in a way that a remote programming session and/or an interrogation session may be performed, a session identifier is generated by the CP or by the RMS. The session identifier is unique to the remote programming and/or interrogation session and is comprised in every data communication packet associated with the remote programming and/or interrogation session. The session identifier is used by the CP, RMS, PR and/or implantable device to associate and verify a communication data packet to the remote programming and/or interrogation session. A new session identifier is generated for every new remote programming and/or interrogation session.

According to an embodiment of the present invention, a session identifier is discarded if the communication connection between the CP and the medical device is lost. A new session identifier is generated when the communication connection between the CP and the medical device is reconnected. Preferably, after reconnecting the communication connection between the CP and the medical device, a remote programming session and/or interrogation session is declared valid if the new session identifier is different from the first (i.e. discarded) session identifier. For instance, the PR is configured to verify whether the new session identifier is different from the discarded session identifier. A reestablished remote programming and/or interrogation session after a reconnection may be declared valid if the new session identifier is different from the first (discarded) session identifier, and/or the reestablished session is declared invalid if the new session identifier is identical to the first (discarded) session identifier.

Moreover, according to an embodiment of the present invention, the PR is configured to attempt a reconnection between the PR and the medical device in case of a connection loss of the third communication connection. For example, the PR is configured to attempt a reconnection between the PR and the medical device if the first and second communication connection are not lost. According to an embodiment, the PR is configured to attempt a reconnection between the PR and the medical device after detecting that, after a reconnection, the new session identifier is faulty (e.g. identical to a first, discarded session identifier). Alternatively or in addition, the PR is configured to attempt a reconnection to the medical device when the PR receives a new session identifier from the RMS.

According to a preferred embodiment of the present invention, the PR is configured to automatically transmit data associated with the medical device to the RMS upon at least one trigger event. For instance, a trigger event is at least one of:

- initiation of a remote programming session and/or interrogation session of the medical device,
- activation of an internal device software of the PR for establishing the second or third communication connection,
- establishing or changing the third communication connection,
- reconnection of the communication connection between the CP and the medical device,
- an information update is requested via the CP,
- a change of information relevant to the remote programming session and/or interrogation session of the medical device.

For instance, according to embodiments of the present invention, regular syncing of the information available or originated by the PR with the RMS is necessary, in particular, information of importance to a remote programming and/or an interrogation session of the medical device, as e.g. the stimulation amplitude for the patient. Some information needed for remote programming and/or an interrogation session of the medical device changes very frequently. Thus, the RMS needs to be frequently updated in order to provide the said information to all crucial participating devices as fast as possible, i.e. in near real-time. Therefore, an information update rate as used by commonly known implantable device remote monitoring platforms (e.g. once per day), is not sufficient to provide a continuous remote programming/interrogation experience. For the purposes of a remote programming and/or interrogation session according to the invention, the information important to the remote programming and/or interrogation session of the implant needs to be available and up-to-date at the beginning of the session for the respective participating devices and systems (i.e. PR, RMS and CP). For example, the information is continually updated during the session for enabling the user of the CP to see the latest stimulation amplitudes and changes of the amplitudes for the patient on the CP in real time. According to an embodiment, "continually updated" may mean to automatically initiate a synchronization of the PR information with the RMS (i.e. the PR initiates a transmission of the information in its local database to the RMS database) based on a trigger event, as said before. Immediately after persisting this state in its local database, the PR also transmits the new state to the NSC database. Further specific examples of trigger events are:

At the start of a remote programming session

- when an application on the PR for establishing a remote programming session launches
- when Bluetooth Low Energy (BLE) connection status between PR and implantable device changes
- when the PR associates with a patient and an implantable device
- when network connectivity is restored after being offline
- when the user (e.g. physician using the CP) taps the function 'Setting/Advanced/Refresh' on the CP user interface Every time new data is generated, e.g.:

- a) on the reception of a remote monitoring or remote programming message from an implant
- b) on any change to a parameter relevant to remote programming (e.g. stimulation parameter change on the implant, like stimulation amplitude)

The system components are specified (e.g. memory, processing capability, transmission speed, etc.) such that they can perform within the boundary requirements of the connectivity use case of the particular embodiment.

According to the present invention, a computer program product is proposed comprising instructions which, when executed by at least one processing unit, cause the at least one processing unit to perform the steps of the method and embodiments of the method presently described.

Moreover, the present invention incorporates a system comprising at least one medical device, a remote monitoring server (RMS), at least one patient remote device (PR) and at least one health care professional (HCP) remote device (CP). The system is configured such that for programming and/or interrogation of one chosen medical device, one CP establishes a communication session connecting the one CP via the RMS and the PR with the chosen medical device using the one CP by establishing a first bidirectional communication connection of the one CP and the RMS, triggering the RMS to establish a second bidirectional communication connection of the RMS and the PR corresponding to the chosen medical device and to establish a third bidirectional communication connection of the PR corresponding to the chosen medical device and with the chosen medical device. The system is configured to provide real-time remote programming and/or interrogation of the chosen medical device using the one CP via the RMS and the corresponding PR, and to maintain the first, second and third communication connections as continuous communication connections. The CP is configured to optimize an internal device process such that the first communication connection can be maintained as continuous communication connection. Alternatively or in addition, the PR is configured to optimize an internal device process such that the second and/or third communication connection can be maintained as continuous communication connection.

Moreover, according to an embodiment of the inventive system, the CP and/or the PR is configured to optimize an internal device process by at least one of:

- reducing the number of internal device software applications and/or reducing an internal device access to software applications to those required for maintaining the first communication connection as continuous communication connection,
- reducing internal device data traffic to that required for maintaining the first communication connection as continuous communication connection,
- reducing internal device communication applications to that required for maintaining the first communication connection as continuous communication connection.

According to exemplary embodiments of the present inventive system, necessary software applications may be those for connection and communication with the RMS, software applications associated with the operating system and/or the Mobile Device Management (MDM) provider, etc.

For instance, for reduction of software applications or for a reduction of an access to software applications:

No internet browser is installed in the PR and/or CP, or a browser is installed, but the browser selection and the list of acceptable URLs is controlled by the MDM system, and/or The internet resources of the PR and/or the CP may be whitelisted to only those resources that are needed for said purpose, and/or The access of the PR and/or the CP to an app store (e.g. Microsoft Store, Google Play Store) may be limited to a reduced set of apps, e.g. privately published apps, and/or Messaging and phone apps of the PR and/or the CP are disabled.

According to a preferable embodiment of the present invention, the RMS is configured to initiate delivery of a notification from an external messaging provider to the PR for establishing the second communication connection between the RMS and the PR. In an example, the external messaging provider is a push notification messaging provider. For instance, the PR, upon receiving the notification, is configured to start polling information from the RMS at a predetermined rate.

Moreover, according to an embodiment of the inventive system, the PR is configured to automatically transmit data associated with the medical device to the RMS upon at least one trigger event. For instance, a trigger event is at least one of:

initiation of a remote programming session and/or interrogation session of the medical device, activation of an internal device software of the PR for establishing the second or third communication connection, establishing or changing the third communication connection, reconnection of the communication connection between the CP and the medical device, an information update is requested via the CP, a change of an information relevant to the remote programming session and/or interrogation session of the medical device.

The system is according to preferable embodiments of the invention, configured to perform the steps of the inventive method, and embodiments of the inventive method.

Moreover, according to further embodiments of the invention, a system is proposed comprising at least one medical device, a remote monitoring server (RMS), at least one patient remote device (PR) and at least one HCP remote device (CP), i.e. a remote device for an HCP, wherein the system is configured such that for programming and/or interrogation of one medical device chosen, for example, by an HCP, one CP establishes a communication session connecting the one CP via the RMS and the PR with the chosen medical device using the one CP by establishing a first bidirectional communication connection of the one CP and the RMS, automatically triggering the RMS to establish a second bidirectional communication connection of the RMS and the PR corresponding to the chosen medical device and to establish a third bidirectional communication connection of the PR corresponding to the chosen medical device and the chosen medical device, wherein the system is configured to provide real-time remote programming and/or interrogation of the chosen medical device using the one CP via the RMS and the corresponding PR, and to maintain the first, second and third communication connections as continuous communication connections (i.e. the connections stay open and active), in one embodiment until a close signal is sent from the one CP to the chosen medical device via the RMS and the corresponding PR. Further, the CP may trigger the communication session.

The proposed method and system have the advantage that communication is provided in real time, via individual system devices automatically interacting in order to facilitate a continuous data stream. The system described further provides HCPs continuously with up-to-date information about their patients while the patients are going about their daily lives. The reduced latency and increased availability of longitudinal data (i.e. data that tracks the same sample at different points in time) provided is expected to result in improved quality of care for the patients and efficiency in the clinic workflow.

The method and system according to embodiments of the invention provide real-time, remotely triggered data update from and remote communication to the medical device. The system comprises an integrated network of the at least one medical device, for example an implanted medical device (IMD), the at least one patient remote device, e.g. a transceiver and/or therapy control device, with a patient user interface (UI), the RMS forming a service centre comprising a central processing (and optionally admin) unit, and the at least one CP as an HCP device (e.g. a computer, a tablet or a notebook, also called programmer) with a HCP user interface (CUI) for remotely programming the medical device. The mentioned system components may communicate via public communication networks. Remote programming according to the invention realizes the use of a CP with a live connection to the RMS and the PR and the medical device.

The method and system may be used for triggering a real-time interrogation of the patient's medical device current data, for remote analysis of current and historical patient data, and for remote communication to the medical device, all done during a continuous session between the HCP user interface (CUI) and the medical device. According to the invention, the system and method system may also be used for remote programming of the medical device.

The invention may be used in multiple areas of medical device application, e.g. spinal cord stimulation (SCS), cardiac rhythm management (CRM), and many other medical fields that utilize an implanted medical device e.g. deep brain stimulation (DBS), occipital nerve stimulation (ONS), trigeminal nerve stimulation (TNS), vagal nerve stimulation (VNS), phrenic nerve stimulation, gastric electrical stimulation, and sacral nerve stimulation (SNS).

The inventive system autonomously manages the elements of the system to:

Ensure the highest possible connected uptime and throughput during a transmission session;

Reduce data transmission latency to effectively zero as far as the end user experience is concerned;

Increase data transmission rate when needed;

Reduce impact to the medical device size of the remote connectivity components;

Reduce impact to the medical device battery longevity of the remote connectivity process.

Enhancing the user experience by simulating a face-to-face interaction, requiring nearly zero latency, leading to increased quality of care, increased patient satisfaction and increased clinician satisfaction.

If the inventive method and system is used for remote programming and/or interrogation of an implantable spinal cord stimulation (SCS) device, it specifically provides the advantages of:

- Increased communication speed and responsiveness leads to better/earlier intervention, reducing the likelihood of pain "wind-up", i.e. pain cycle causes physiologic remodeling that can occur when care for new pain vectors cannot be provided quickly.
- Increase availability of data access, improve SCS trial outcomes via improved optimization, improve clinic workflows, and reduce travel demands on patients to achieve desired care.
- Reduced latency between steps leads to reduced overhead time for clinical staff, thereby reducing overhead cost.

The following features are also/may also be implemented in any combination with each other:

- HCP-triggered request for the interrogation of the chosen medical device.
- The HCP-triggered request of the interrogation may be initiated remotely, from one or more CUI, e.g. (1+N) CUI where N is a natural number; N=0, 1, 2, . . . .
- The data collected by the interrogation may be viewed remotely at (1+N) UI or CUI.
- Data derived from interrogation are a combination of subjective and objective data.
- Data derived from interrogation are a combination of current and historical data.
- Data presented is collected from (1+N) Data Reporters (N-natural number; N=0, 1, 2, . . . )

In one embodiment, one or more (e.g. all) steps in the sequence of establishing communication connections may require a "handshake" process that may 1.) ensure cybersecurity and 2.) provide automatic data persistence, communication persistence and communication repetition to ensure that the communication between each component is completed.

As indicated above, the inventive system comprises at least the following components:

- At least one individual-patient medical device, for example an IMD, also known as "therapy device";
- A Remote Monitoring Server (or RMS), for example a "Neuro Service Center" (NSC) in one embodiment. The RMS is, for example, a hardware and/or cloud-based service center that facilitates Remote Programming (RP) and data interrogation of the at least one medical device, and may comprise a central data repository of data collected by the at least one CP, the at least one PR and/or the at least one medical device, wherein the hardware may comprise at least one computing device or a network of a plurality computing devices, wherein the RMS further comprises the computing functionality described herein; the RMS is a functional unit that performs substantial computations, including numerous arithmetic operations and logic operations without human intervention and may comprise, such as, for example, a desktop computer, a server computer, clusters/warehouse scale computer or embedded system;
- At least one Patient Remote (PR) that serves as a transceiver to route communication between the medical device and the RMS, and to provide to the patient some aspect of local control of the therapy process. For example, it gives the patient the ability to change the active therapy program of a medical device, for example a medical device for SCS, control its stimulation amplitude, turn stimulation on/off, and view battery status. It may also serve as an external programmer for the medical device;
- At least one HCP device/programmer (CP) used by HCPs or field technical representatives to program the medical device remotely. The CP may be physical (i.e. dedicated device) or virtual (e.g. via web-based interface to the system, secure connected data reporters).

For communication, public communication network(s) (PCN) is (are) used and in each CP an HCP device user interface (CUI), e.g. GUI at the physical CP or web portal at virtual CP, and in each medical device a PR user interface (UI). The RMS may further manage deployed at least one PR and at least one CP, which are together called external programmers (EP) in the following.

For data/signal processing each of the CP, RMS, PR, medical device comprises at least one processing unit which is generally regarded as a functional unit of the respective component, that interprets and executes instructions comprising an instruction control unit and an arithmetic and logic unit. The processing unit may comprise a microprocessor, a controller, a digital signal processor (DSP), an application specific integrated circuit (ASIC), a field-programmable gate array (FPGA), discrete logic circuitry or any combination thereof. Alternatively, or additionally, the processing unit may be realized using integrated dedicated hardware logic circuits, in case of a medical device due to the small size and extreme power limitation.

Each component may further comprise a data memory which may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The data memory may, for example, store buffer data of the respective component as described below.

The medical device may comprise at least one detector detecting at least one bodily parameter of the patient. The detector is connected to the processing unit for processing the determined bodily parameter.

Each component may comprise further units such as a communication unit for communication as indicated in this description and a power supply such as a battery. The communication may occur at least partly extracorporeally. The communication may be provided wirelessly via the patient's body and/or the air using electromagnetic waves, for example Bluetooth, WLAN, ZigBee, NFC, Wibree or WiMAX in the radio frequency region, or IrDA or free-space optical communication (FSO) in the infrared or optical frequency region, or by wire (electrical and/or optical communication).

In particular, the implantable medical device's units may be contained within a hermetically sealed housing.

For remote programming (RP) or interrogation using the CP, in this invention the use of single, serial handshakes between each component of the system is significantly reduced. Each component is designed to autonomously maintain a continuous connection to its respective neighbours, via an on-going session that persists for the duration of the RP or interrogation process, wherein the medical device has bidirectional communication link to the PR, the PR has a bidirectional communication link to the RMS and the RMS a bidirectional communication link to the CP, for example

- Medical device and PR maintain, for example a Bluetooth connection while they are in proximity.

PR and RMS maintain, for example a TCP/IP network connection over the internet while mobile networks are available.

CP and RMS maintain, for example a TCP/IP network connection over the internet while mobile networks are available.

Further, feedback loops exist between the components to maintain a closed loop of one component with the component adjacent to it in the communication pathway, to proactively assess the status of the communication process and to automatically and immediately process information when received. Each link between one component to the next transmits new data to the next hop in chain as soon as new data is available, thereby reducing transmission latency to (nearly) zero. Additionally, in case of connectivity loss, any system component sends new buffered data as soon as connectivity to the neighbour is restored. The system, i.e. each of the at least one CP, the RMS and at least one PR, comprises a data buffer of sufficient depth to sustain occasional loss of connectivity, and to allow the transmission of large datasets.

Each link releases local data storage as soon as the neighbour has received the data payload.

The process is based upon standard, off-the-shelf communication protocols (e.g. TCP/IP) but the data transmission is controlled by methodologies proprietary to BIOTRONIK and specific to the device application. For example, proprietary data transmission control comprises sending alert notifications to request a data transmission, e.g. from the RMS to the PR;

routing data to the right medical device, whereby topology information (connection between PR and medical device) can be used; and choosing appropriate signature and encryption keys for the receiver of a data transmission.

Component's specifications used will be specific and optimized for each medical device application. For example, the medical device may adjust its data sampling rate based upon the communication bandwidth available to it (communication with PR), the PR may buffer its data transmission to adjust for bottlenecks downstream of it, etc. The concept is similar to the way a video feed over the internet is buffered. In typical modem video transmission, TCP and HTTP are ubiquitous, and most video is accessed over the Web. A video server built on top of TCP/HTTP uses commodity HTTP servers and requires no special hardware or software pieces. In the described process, the components are specific to the particular task, and communication is done via a secured network. The system is designed such that no user adjustment is required during the communication process. Each component in the system may automatically optimize its behaviour within a proscribed range to match the current communication capability.

This results in a system as indicated above. At first, the HCP triggers the communication session at the CP using CUI via a session request that is sent to the RMS. In one embodiment, the start of the session provided by the HCP is triggered by the medical device, RP or the patient. For example, upon the observation of a pathological situation by the patient, the medical device or the RP may initiate a signal comprising the respective information which is then sent by the respective component to the RMS and the HCP. Based on this information, the HCP may trigger the communication session at the CP as described above. Then, the RMS automatically initiates a session with the PR. Handshake with the PR is completed and communication between the two components persists. Afterwards, the PR automatically initiates a session with the IMD. Handshake with the medical device is completed and communication between the two components persists. The medical device then sends an acknowledgement response to the HCP via the PR-to-RMS-to-CP communication chain. Session is established, with all components now connected in real-time. Now, the remote programming may be provided to the medical device and/or data may be interrogated from the medical device using the established and continuous communication chain. Upon completion of the use case, the session initiator indicates that the session is complete and signals the other components to release their handshakes. Throughout this process, only one handshake is required between adjacent components, each communication channel stays open and steady until a closing message is sent, which closes all connections between the devices.

With each system component passing on the data payload from the device upstream from it as fast as it is received, and refreshing its memory buffer continuously to enable receipt of new data, the information as viewed at the CUI is that of a continuous stream, rather than individual packets of information, and is received with very low latency (i.e. similar to a phone call). Compared to the analogy of "a picture taken and sent via text message "for state-of-the-art IMD systems of sporadically connected sub systems, this invention provides a "video conference" where data is streamed between the medical device and the CP (and thereby via the CUI the HCP) for the duration of the session.

The RMS may be hosted by a service provider, e.g. a company external from a clinic. The RMS may comprise at least one of the following services:

Repository of data collected by EP and medical devices;

Repository of keys and certificates for communication of the elements of the system and the HCP or patient via UI or CUI with the system Facilitates remote programming by routing data to/from their intended destinations;

Communication with at least one external push notification service;

CP fleet management (e.g. via Airwatch and processes to manage CPs);

Medical device instance authentication service;

HCP, technician and patient authentication service; and

Database analytic tools.

As indicated above, the RMS may serve as a repository of data collected by EPs and medical devices. The latter may comprise home monitoring (HM), which originates from the medical device and is routed to the RMS via the PR. In one embodiment the HM data may be encrypted by the medical device and may only be decrypted by the RMS. In this embodiment, the PR does not have any key to decrypt the data. RMS's "certificate and key management system" (CKMS) may be used to decrypt the data.

Further, after the above mentioned communication connections are established from the CP to the chosen medical device as indicated above, the RMS is used as the conduit to route RP commands from the CP to the medical device and/or return responses and status updates from the medical device to the CP.

A hardware and/or cloud server (e.g. Couchbase® server) may be used to store the data in the RMS. The RMS notifies EPs to pull data from the server via push notifications. RMS sends a push notification request to an external notification service (i.e., Microsoft Azure, Google Firebase Cloud Messaging), which in turn is sent to a specific EP.

A subset of data is copied from the RMS to a data warehouse to support internal business functions such as technical forensics, quality monitoring, and clinical studies.

CKMS may be used to generate and store secrets for every manufactured medical device. Secrets, e.g. encryption keys and authentication credentials, are generated during manufacturing and stored into the medical device. Generated secrets are used to cipher data when:

- Remote programming data is sent from the RMS to the medical device;
- HM data are sent from the medical device to the RMS.
- RMS uses an authentication management and access service, e.g. Keycloak, for PR authentication. During provisioning, a PR creates a username and password on the authentication management and access service. Subsequently, PRs submit their credentials to the service for an access token, for example, based on JSON Web Token (JWT). The token is then presented to RMS Sync Gateway to gain access. This follows the OAuth 2.0 authorization code grant model. OAuth is an open standard for access delegation, for example, used as a way for Internet users to grant websites or applications access to their information on other websites but without giving them the passwords.

The RMS may provide CP user management and authentication using a Microsoft Azure Active Directory (AAD) which may be integrated in the RMS or may be realized as an external unit connected with the RMS. In the latter case, the RMS interacts with AAD for HCP and patient management operations.

In one embodiment, CPs may follow the OAuth 2.0 authorization code grant model to gain access to the RMS, where AAD acts as the authorization and token endpoints. Once authenticated, the CP is given an access token, which in turn passes to RMS Sync Gateway to gain access.

Medical devices may send/receive data to/from the RMS, via the PR, such that the PR may not decipher the data. Each medical device has unique keys assigned to it at the time of manufacturing.

EPs may communicate to the outside world via either Wi-Fi or cellular network. This introduces a large attack surface that may impact the EP-to-medical device programmability.

However, CPs may be protected by the following:

- Malware protection and firewall (e.g. Windows Defender malware and firewall).
- CP users are granted user rights and thus not able to install software.
- Internet resources are whitelisted to resources that are needed for its functionality (e.g., NSC, Microsoft, MDM provider, etc.)
- Access to other internet resources, such as Microsoft Store, is inhibited or limited to privately published apps.

PRs may be protected by the following:

- No internet browsers installed.
- Messaging and phone apps disabled.
- Access to other internet resources, such as Google Play Store, is inhibited or limited to privately published apps.

In one embodiment, Couchbase® may be used as the database engine used to store and share data in the RMS. EPs may use Couchbase Mobile, and the RMS may use Couchbase® Sync Gateway and Couchbase® Server. This setup allows for data replication between the mobile client (EPs) and the RMS.

On the PR, information may be stored, e.g. in the Couchbase® instance, pertaining to the medical device, which is associated with such aspects as therapy program settings, battery state of charge (SoC), connection state, etc. This data, in turn, is replicated at the RMS.

In one embodiment, when CPs command a change(s) to a target medical device, i.e. a remote programming, the changes are packaged, placed into the local database instance (e.g. Couchbase® instance), and pushed to the RMS. Once received by the RMS, the package is encrypted then authenticated by CKMS using the target medical device's pre-shared secret keys. Because the medical device's shared secret key is only known by CKMS and the medical device, the PR is not able to decipher the package's contents. The PR receives the remote programming package after it has finished synchronizing with the RMS Server.

In one embodiment data transmission between EP and RMS is encrypted, as well as the BLE link between the EP and medical device. For example, a 2-factor authentication is used when the CP user (e.g. the HCP) selects a chosen patient's medical device to remotely program. In one embodiment, the RMS is configured to store and/or manage the authentication and/or encryption keys and/or certificates for the at least one CP, at least one PR, at least one medical device as well as for the at least one user of the system, for example, patient, HCP and/or technician. For that, the RMS may integrally comprise hard- and/or software solutions for that or the RMS may be connected to respective hard- and/or software solutions. For example, Microsoft Azure may be responsible for managing this on the backend, and Microsoft APIs may be responsible for managing user input on the CP side (i.e., login mechanism, communication with Azure, handling of 2-factor input, etc.).

In one embodiment, once the CP user has been authenticated, an authentication service of the system returns one unique signed token, e.g. the above mentioned JWT token, to the CP (referred to as the remote programming session token). The CP provides this token to the RMS during every remote programming transaction during the remote programming session. The one unique token is valid for the duration of the current remote programming session; subsequent remote programming sessions require a new unique token, which means the HCP having to go through the authentication sequence again. Using such tokens allows decentralizing authentication and authorization.

In one embodiment, the at least one PR may be not configured to continuously poll the RMS for changes, as that would result in unnecessary overhead on both the PR and RMS (i.e., data usage from the PR's perspective and request processing from the RMS's perspective). Instead, the RMS may interface with an external push notification system, such as Google's Firebase Cloud Messaging system, to send a notification to the target PR corresponding to the chosen medical device. Conceptually, for example, prior or at the beginning of establishing a communication connection or at the beginning of the remote programming session the target PR receives a push notification from the RMS. This notification serves as a trigger to the PR to poll the RMS server at a faster rate. In one embodiment, the notification does not contain detailed information, such as any identifying or secret data.

In one embodiment, remote programming session begins with the CP user (e.g. the HCP) logging into their CP. Regardless of a session type, all CP users must log in. After logging in, the CP user will be able to select the option to start a remote programming session, which will present them with a list of patients they may remotely program.

From a hierarchal standpoint, patients may be organized by their clinic. CP users may be associated with one or more clinics. Therefore, CP users may only remotely program patients' medical devices for clinics that they are associated with.

In one embodiment, 2-factor authentication is required to be provided when the CP user (e.g. the HCP) selects a patient to remotely program. For example, Microsoft Azure may be responsible for managing this on the backend, and Microsoft APIs may be responsible for managing user input on the CP side (i.e., login mechanism, communication with Azure, handling of 2-factor input, etc.). The CP is responsible for sending a request to authentication service to gain access to the remote programming resource. Once the user has been authenticated, the authentication service returns a signed token, e.g. a JWT token to the CP (referred to as the remote programming session token). The CP provides this token to the RMS during every remote programming transaction during the remote programming session. The token is valid for the duration of the current remote programming session.

Once the code has been authenticated, the CP may pull the latest copy of the target medical device's data from the RMS, and the user will be able to proceed with a remote programming session.

In one embodiment, PRs may be not configured to continuously poll the RMS for changes, as that would result in unnecessary overhead on both the PR and RMS (i.e., data usage from the PR's perspective and request processing from the RMS's perspective). Instead, the RMS interfaces with an external push notification system, such as Google's Firebase Cloud Messaging system, to send a notification to the target PR. Conceptually, for example, at the beginning of a remote programming session the target PR receives a push notification. This notification serves as a trigger to the PR to poll the RMS Server at a faster rate. The notification does not contain detailed information, such as any identifying or secret data.

The following data may be transmitted during a remote programming session (i.e. "signals"). Please note that these data will differ dependent upon the embodiment. The following data may refer partly to a remote programming process of an SCS system which is described here as a typical embodiment.

a) Medical Device Data
- Medical device data (serial number, medical device type)
- Therapy data (e.g. therapeutic data (packed parameter values, packed data elements, and interface parameters)), lead impedance, offset measurements, therapy program selection, stimulation on/off, enable/disable MRI mode, battery SoC, status changes, lead info/configuration ("blob" and interface data), medical device alerts, IMD EC App Status, stimulation usage data (used for statistics)
- Personal data (patient name, physician name, hospital, implantation date of the medical device, indication, lead position, lead type and extension information, implanted system component traceable IDs
- Notes
- Patient Identifier (unique ID, serial number of medical device)

b) Technical Data
- Technical data/logs (reset, battery, etc.)
- System-based events
- Battery history log
- MRI mode
- Magnet history
- medical device reset log
- EP application log
- application logs
- Error logs
- Audit logs c) Connectivity Device Data for Communication Protocols (the System Uses the Standard Data Overhead Required for the Following Communication Protocols)
- Bluetooth® Low Energy (BLE) (the medical device radio's transceiver may support BLE 5.0, though the product uses BLE 4.2)
- 4G
- Wi-Fi
- TCP/IP The RMS as configured transmits at least part of these data from the RP while the RMS transfers data with the CP.

In one embodiment, for remote programming of the chosen medical device the CP is configured to produce a single program containing the updates and/or changes of the medical device's parameters and to transmit the single program to the medical device via the RMS and the corresponding PR. This is explained in more detail below. Further, in one embodiment the RMS is configured to encrypt the single program received from the CP, wherein the corresponding PR is configured to transmit the encrypted single program to the chosen medical device. Accordingly, the PR cannot decrypt the single program. Decryption is provided by the medical device as explained in detail below.

In one embodiment, the RMS is configured such that its central data repository comprises data having different security levels, wherein one example of data with a lower security level are pseudonymized data. Data with a higher security level are personal or private data such as names, addresses, user ID etc. These data need higher protection and can only be accessed by persons having a higher security level.

In one embodiment, in order to provide data of the RMS for further analysis or for assessment of efficacy of the therapy of the at least one medical device, the RMS is configured to be connected with a data warehouse and/or a clinical data warehouse, wherein the data warehouse and/or the clinical data warehouse are configured to import at least a part of the data stored in the central data repository. The warehouses and their operation are further explained below.

Management of specific error conditions of the system is explained in the more detailed description below.

Further, the above object is solved by the method for programming and/or interrogation of one chosen medical device of a system comprising at least one medical device, a remote monitoring server (RMS), at least one patient remote device (PR) and at least one HCP remote device (CP), wherein one CP establishes a communication session connecting the one CP via the RMS and the PR with the chosen medical device using the one CP by establishing a first bidirectional communication connection of the one CP and the RMS and automatically triggering the RMS to establish a second bidirectional communication connection of the RMS and the PR corresponding to the chosen medical device and to establish a third bidirectional communication connection of the PR corresponding to the chosen medical device and the chosen medical device, wherein real-time remote programming and/or interrogation of the chosen medical device is provided using the one CP via the RMS and the corresponding PR, wherein the first, second and third communication connections are maintained as continuous communication connections.

In one embodiment, the RMS comprises a central data repository of data collected by the at least one CP, the at least one PR and the at least one medical device.

In one embodiment, prior or during establishing a communication connection between the RMS and the corresponding PR, the RMS sends a push notification to the corresponding PR thereby triggering this PR to poll the RMS at a faster rate.

In one embodiment, the RMS is connected with a data warehouse and/or a clinical data warehouse, wherein the data warehouse and/or the clinical data warehouse import at least a part of the data stored in the central data repository.

The above embodiments of the operation method have the same advantages as the above system. Embodiments of the system indicated above may be realized in the operation method analogously. It is referred to the above explanation of the system in this regard.

The above method is, for example, realized as a computer program which comprises instructions which, when executed, cause the processing units (processors) of the components of the system to perform the steps of the above method which is a combination of above and below specified computer instructions and data definitions that enable computer hardware to perform computational or control functions or which is a syntactic unit that conforms to the rules of a particular programming language and that is composed of declarations and statements or instructions needed for an above and below specified function, task, or problem solution.

Furthermore, a computer program product is disclosed comprising instructions which, when executed by the processing units, cause the processing units to perform the steps of the above defined method. Accordingly, a computer readable data carrier storing such computer program product is disclosed.

The present invention will now be described in further detail with reference to the accompanying schematic drawings, wherein FIG. 1 shows one embodiment of the inventive system and the steps establishing the communication between the components of the system;

In the following, embodiments of the inventive system will be explained in detail. The embodiments are explained with regard to medical devices in the form of spinal cord stimulation (SCS) devices and a remote monitoring server (RMS) in the form of a Neuro Service Center (NSC) and with regard to remote programming which may include data interrogation.

Figure 1:
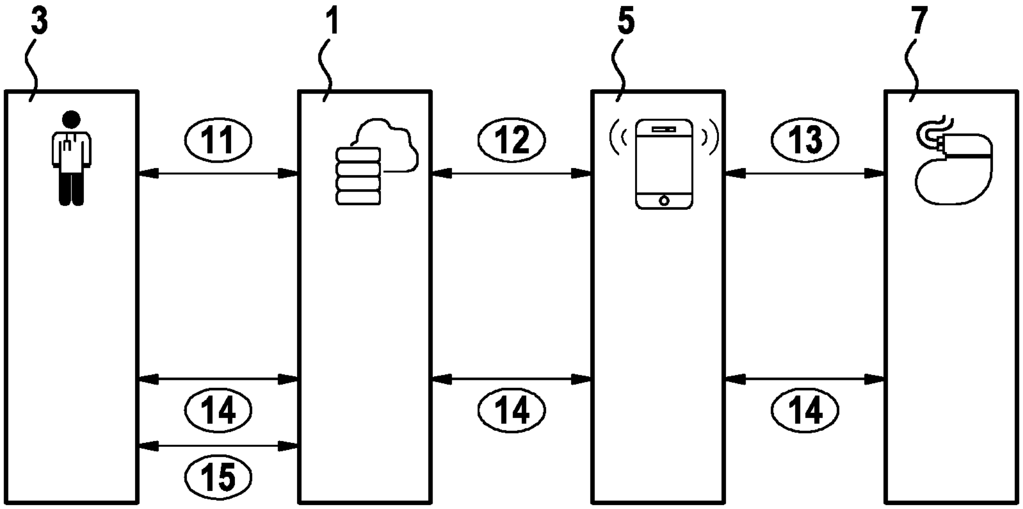

FIG. 1 shows the components of the system, namely the RMS 1, which is, for example, the NRS, at least one HCP remote device (CP) 3, at least one patient remote device (PR) 5, and at least one medical device, for example an SCS device, 7. For further information and for the properties with regard to the system components 1, 3, 5, 7 it is referred to above explanation in the general description.

An overview of the remote programming (RP) method may be derived from FIG. 1 comprising the following steps. At first, the HCP triggers the communication session at his/her UI (CUI) at the CP 3 by a session request 11 which is sent to the RMS 1. Then, the RMS initiates a bidirectional communication connection 12 with the PR 5 based on a handshake with the PR 5. In the next step, the PR 5 initiates a bidirectional communication connection 13 with the medical device 7 based on a handshake process, as well. Then, the medical device 7 sends a response to the CP 3 via the PR 5 to RMS 1 to CP 3 communication chain which is denoted in FIG. 1 with reference number 14. Now a continuous bidirectional communication connection is established between the CP 3 and the medical device 7 with all components now connected in real-time. Thus, also between CP 3 and RMS 1 a bidirectional communication connection is established, in this case by means of the session request 11. All the mentioned bidirectional communication connections can also be established in other ways than by means of the session request 11. Upon completion of the use case, the session initiator (HCP) indicates at CP 3 that the session is complete and signals the other components to release their handshakes (step 15). Throughout this process, only one handshake is required between adjacent components, each communication channel stays open and steady until a closing message is sent which closes all connections between the components.

In one embodiment the following protocols may be used:

Medical device 7 to PR 5: Bluetooth Low Energy (BLE)

PR 5 to public communication network(s) (PCN), e.g. 4G LTE, WiFi 802.11

PR 5 to RMS 1: TCP/IP

RMS 1 to public network(s): VPN

RMS 1 to CP 3: TCP/IP

Accordingly, the system components of this embodiment and other embodiments may comprise interface modules to communicate via mobile wireless networks (e.g. SMS connection, GPRS data connection, UMTS data connection, LTE data connection), virtual private network(s) or dedicated line(s), internet and local networks via Ethernet or WLAN, electronic patient/case files (electronic medical records) via HL 7 v2 or v3 or similar. Further, suitable communication standards e.g. TLS+TCP/IP, SSL+TCP/IP or ebXML may be used.

Figure 2:
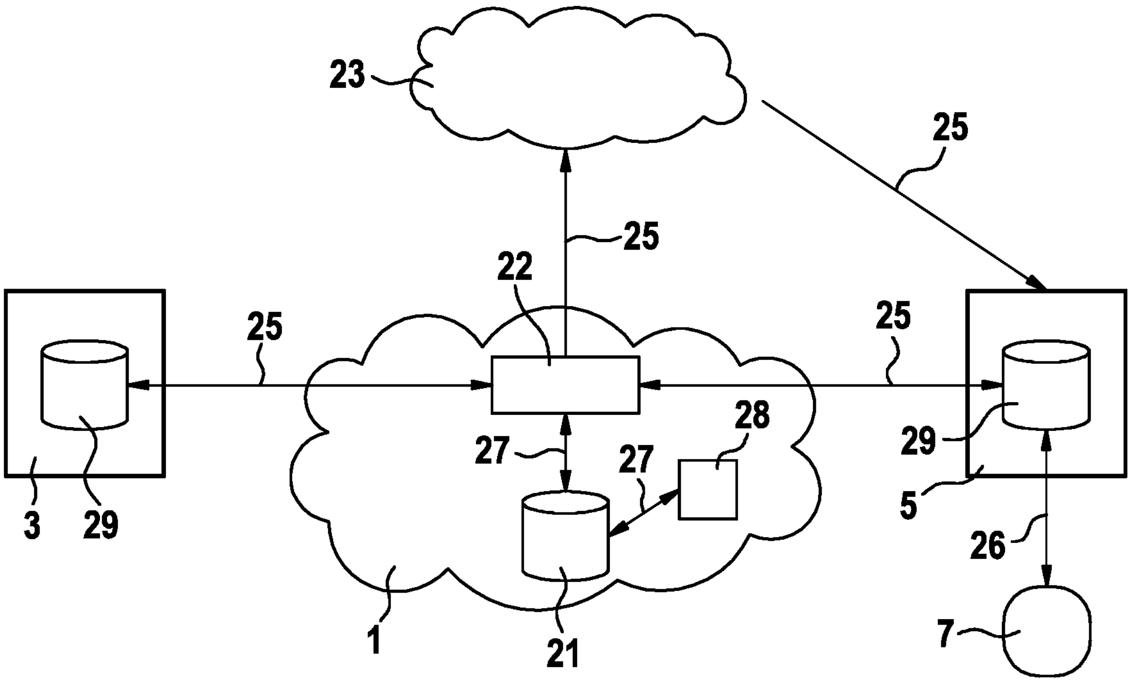
FIG. 2 depicts another sketch of the inventive system.

FIG. 2 contains a different visualization of the whole inventive system. The RMS 1 comprises a Couchbase server 21 as central data repository to store data. Additionally, RMS 1 comprises a Couchbase Sync Gateway 22 for synchronization and communication with CP 3 and PR 5. The system further comprises External Push Notification Services 23 (e.g. Microsoft Azure, Google Firebase Cloud Messaging) in order to notify the CP 3 or the PR 5 to pull data from the RMS 1 via push notifications. For that, the RMS 1 sends a push notification request to the external push notification services 23. In FIG. 2 the arrows 25 represent Internet connections, the arrow 26 a BLE connection and the arrows 27 local network connections (e.g. LAN connections). The RMS 1 further comprises a certificate and key management system (CKMS) 28 which is used to decrypt the data received from the at least one medical device 7. In one embodiment the External Push Notification Services 23 may be integrated in the RMS 1. Further, in order to communicate with the Couchbase server 21 of the RMS 1 the CP 3 and the PR 5 each comprises a Couchbase mobile application 29.

Figure 3:
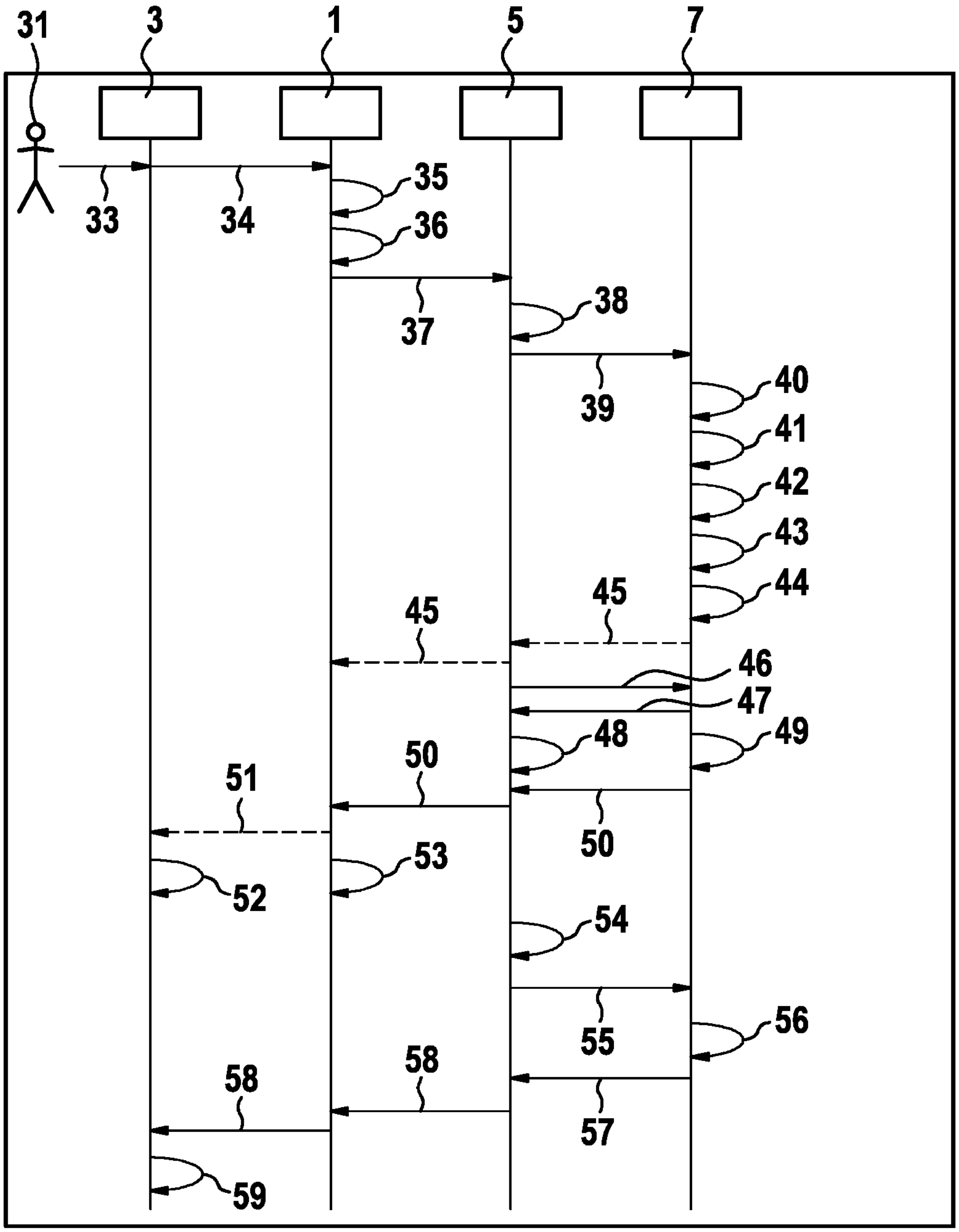
FIG. 3 shows a remote programming overall workflow.

FIG. 3 shows an overall workflow for remote programming which is explained in further detail in the following. The workflow for remote programming works provided the continuous communication connection is previously established between the CP 3 and the medical device 7 after selection of a specific patient/medical device 7 for remote programming. The sequence of events starts with the CP user (e.g. an HCP) commands the transmission of a therapy program using remote programming. As indicated below, the therapy program contains all changes/updates of the parameter of the medical device 7 which are to be programmed. The method describes the process uplink and downlink.

At first, after authentication of the HCP 31 at his/her CP 3 the HCP 31 configures a new therapy program for the patient to be used at its medical device 7. Then, after pressing the transmit button (step 33) the therapy program is transmitted to the RMS 1 (step 34). At the RMS the access token is verified (step 35) and a remote package containing the information of the therapy program is ciphered (step 36). This remote package is then transmitted (automatically, i.e. without further HCP or patient interference) to the PR 5 (step 37). In the next step, the patient is prompted about the fact that there is a therapy program arrived at his/her PR 5 (step 38). In the next step 39 the patient accepts the therapy program and the ciphered remote package is automatically sent to the medical device 7. The remote package is not deciphered at the PR 5 but at the medical device in step 40. In step 41 the therapy program is saved to a buffer of the medical device 7. Step 42 comprises ruling a check to the therapy program in medical device 7 and step 43 and installation and activation of the therapy program. Additionally, in step of 44 the medical device 7 generates and ciphers a remote acknowledgment signal which is to be sent to the RMS 1.

Then, using the continuous communication connection to the RMS 1, the encrypted acknowledgment signal is returned to the RMS 1 via the PR 5 (see steps 45).

Additionally, the PR 5 may automatically interrogate the medical device 7 for new data. This is facilitated in step 46, wherein this step contains an interrogation request to the medical device 7. This interrogation request may be sent via the continuous communication connection between the PR 5 and the medical device 7. In response to this request in step 47 the medical device 7 provides the PR 5 with its interrogation data. Then, in step 48 the PR 5 updates its graphical UI. At the same time the medical device 7 generates and ciphers HM PGMR frame in step 49. The PGMR frame contains detailed parameter values programmed in the medical device. In step 50 the PGMR frame is returned to the PR 5 and routed to the RMS 1. Here, the authenticity of the programmed parameter values can be checked. In the next step 51 the latest therapy entities may be pulled to the CP 3. Then, in step 52 the CUI of the CP 3 is updated and at the same time in step 53 the PGMR frame deciphered, data assembled, PPVs unpacked and PDEs as well as appropriate entities at the RMS 1 updated. This allows to check the success of the remote programming procedure on the CP and to give feedback to the HCP via the CUI.

In the next step 54 further adjustment of the medical device 7 may be provided by the PR 5, for example, in the case of an SCS a global amplitude may be adjusted. A respective signal, for example, to adjust the medical device's program stimulation amplitudes and to save the global amplitude may be sent to the medical device 7 in step 55. The respective action is provided by the medical device in step 56. In step 57 a response is sent from the medical device 7 to the PR 5 returning stimulation amplitudes. The following steps 58 returns the latest status of the PR 5 to the RMS 1 and the CP 3. Finally, in step 59 the CUI the of the CP 3 is updated accordingly.

In the process described with regards to FIG. 3 the steps 34, 37, 51 and 58 may be Couchbase, commands and responses. Further, the steps 39, 45, 50 may be provided as end-to-end encrypted commands and responses.

Figure 4:
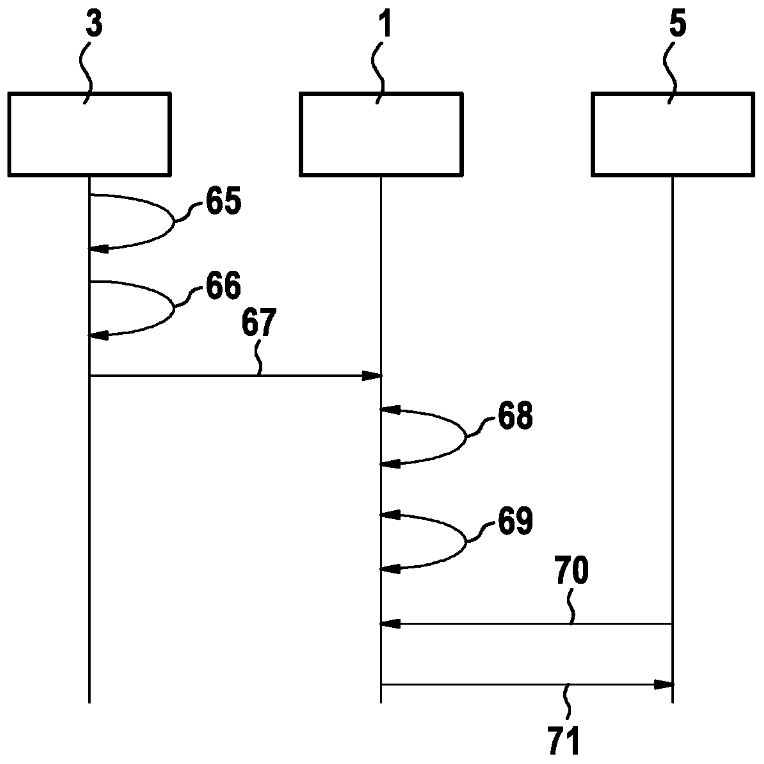
FIG. 4 shows the flow of events for transmission of data to the PR during RP.

FIG. 4 describes the first steps of remote programming using the Couchbase server 21 and Couchbase mobile 29 of the CP 3 in more detail. When CP 3 commands a change to a target medical device 7 (step 65), the changes/updates of the parameters of the medical device 7 are packaged in step 66. Then, they are placed into the local a Couchbase instance by the Couchbase mobile 29 and pushed to the RMS Couchbase sync Gateway 22 and the Couchbase server 21 (step 67). Then, the package or its information is encrypted using the shared keys of the target medical device 7 provided by CKMS 28 (step 68). Because the medical device's shared secret key is only known by CKMS 28 and the medical device 7, the PR 5 is not able to decipher the package's contents. Then, the encrypted remote package is placed into the Couchbase application (step 69). The Couchbase changes are pulled and sent at the next polling interval after it has finished synchronizing with the RMS's Couchbase server 21 (see steps 70 and 71 in FIG. 4).

Figure 5:
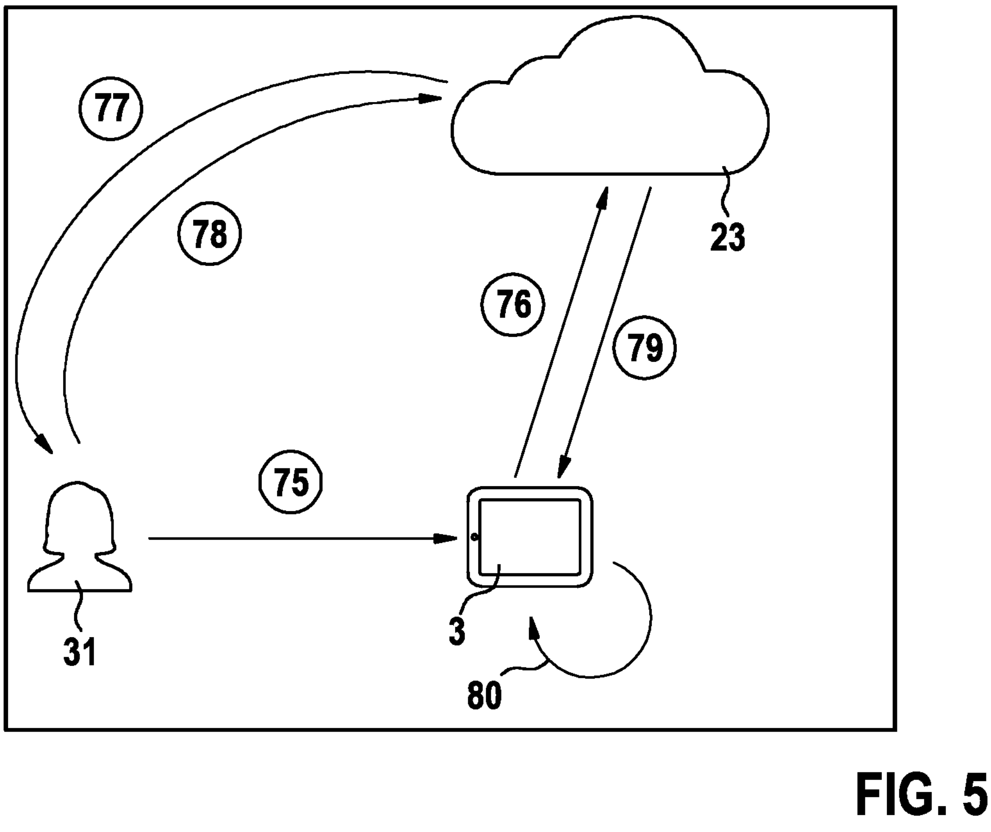
FIG. 5 depicts an example of 2-factor authentication using push notification based approval.

Prior to above programming steps the remote programming process needs to be initiated which is explained in the following with regard to FIG. 5 showing the start of a remote programming (RP) session after the HCP was logging into his/her CP 3.

Patients may be organized by their clinic. HCP, i.e. CP users, may be associated with one or more clinics. Accordingly, it may be defined that a CP user is allowed to remotely program patients medical devices only for such clinics to which they are associated. In one embodiment, a 2-factor authentication is required to be provided if the HCP selects a patient for remote programming. As indicated above, Microsoft Azure may be responsible for managing this on the back end and Microsoft APIs may be responsible for managing user input on the CP side (login mechanism, communication with Azure, handling of second factor input etc.).

Figure 26:
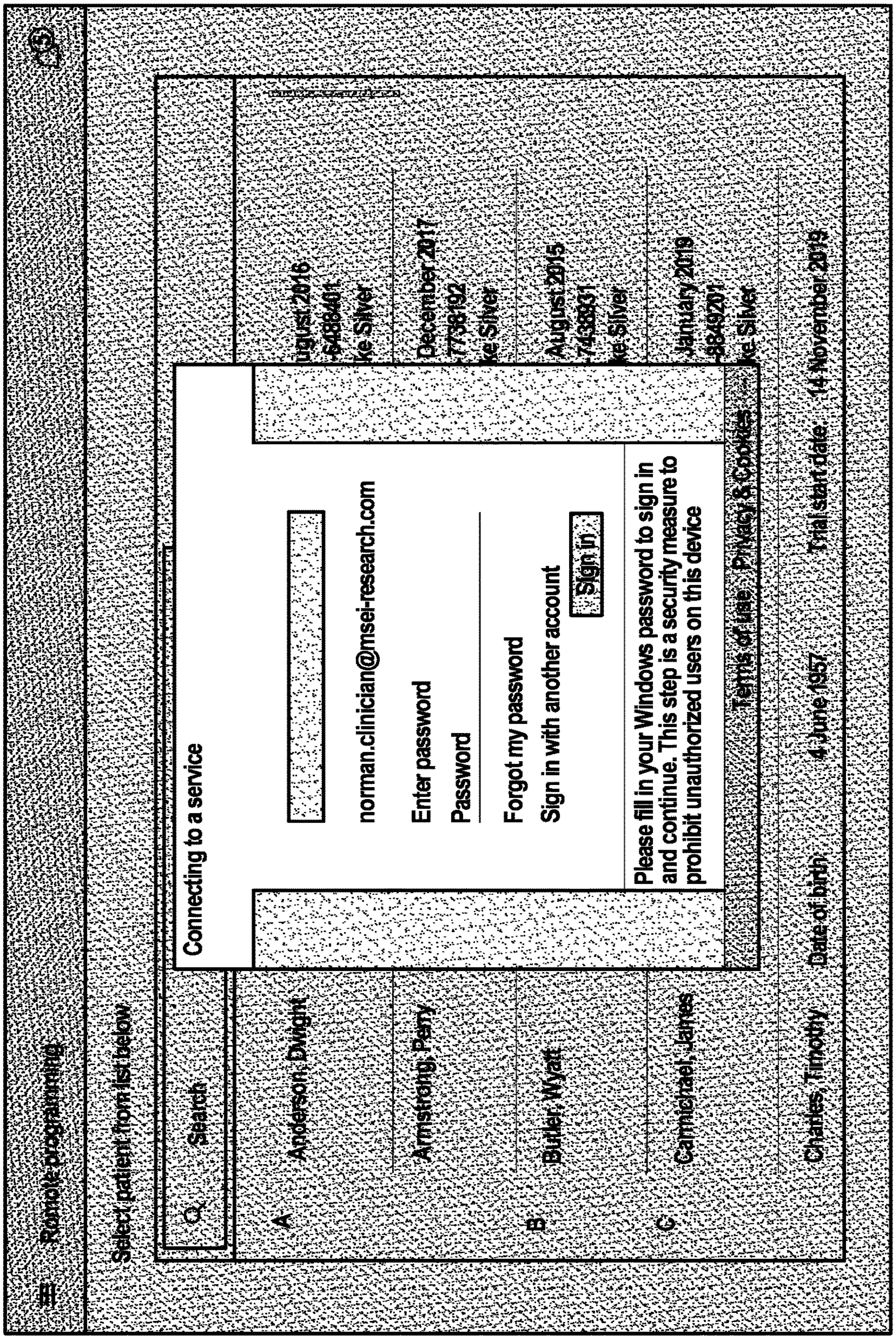
FIG. 26 shows an example of a CP screen during RP (user (HCP) authentication)
Figure 27:
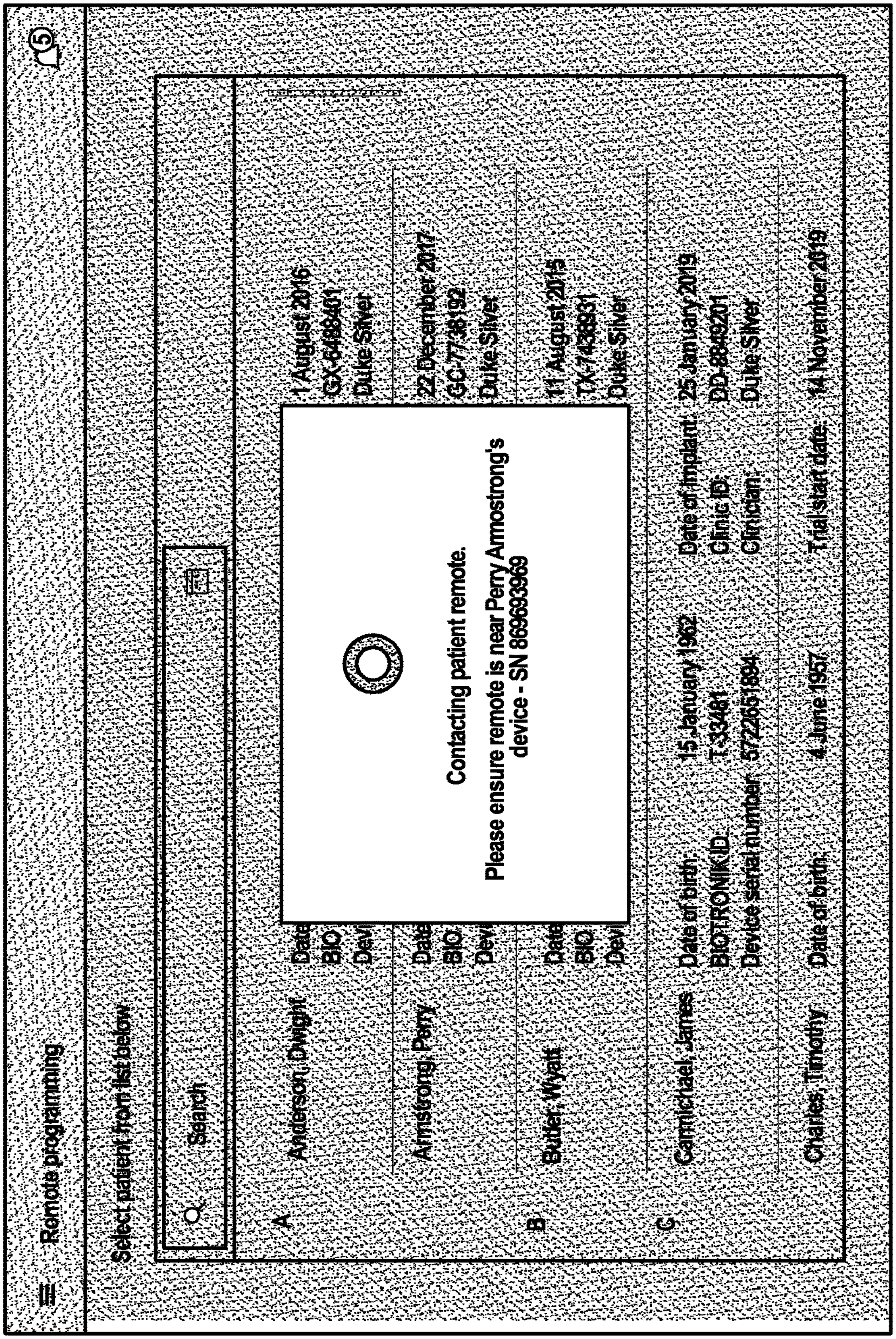
FIG. 27 shows an example of a CP screen during RP (connection status)

The RP session starts with the HCP requesting to start remote programming in step 75 in FIG. 5. Then, in step 76 user credentials are passed for a remote programming token to the external push notification service 23. In step 77 this service sends an authorization request to the HCP's mobile device (see example for user authentication screen in FIG. 26) and in step 78 the HCP 31 accepts the request. Then the external push notification service 23 returns a signed access token to the CP 3 in step 79. The process then continues with remote programming (step 80).

Figure 6:
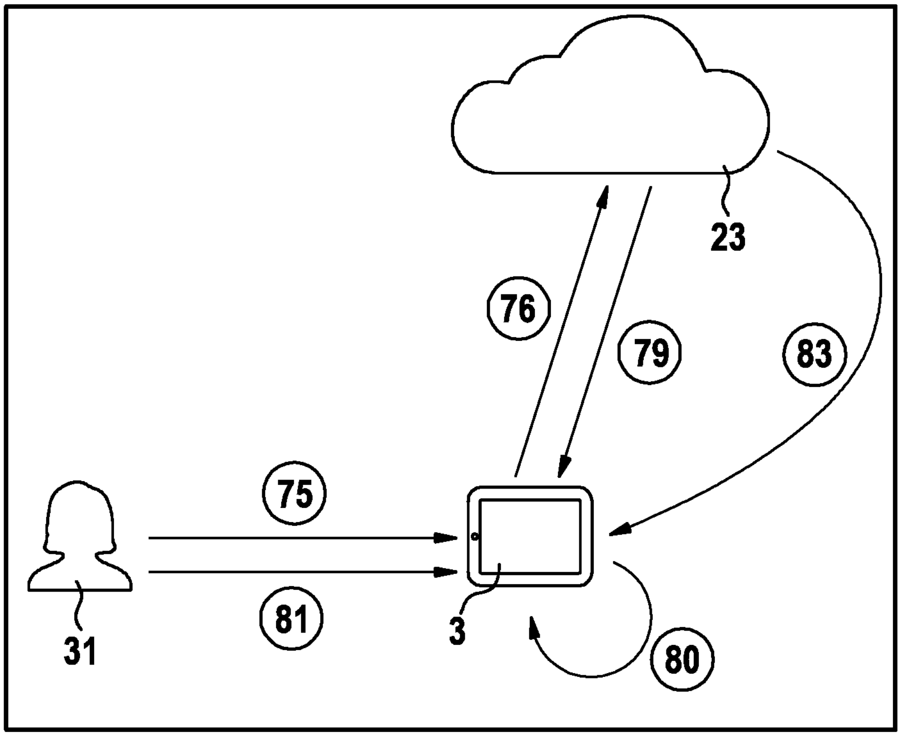
FIG. 6 shows a 2-factor authentication using a 6-digit code (TOTP)

Alternatively, a 2-factor authentication as described with regard to FIG. 5 may be provided using a 6-digit code (TOTP). This is described with regard to FIG. 6. The steps 75 and 76 are identical to the same steps explained with regard to FIG. 5. In the next step 81 the HCP enters a 6-digit code from an authenticator application on his/her mobile device. In step 82 this 6-digit code is passed from CP 3 to the external push notification service 23 via a Microsoft supplied web interface. Then, if this 6-digit code is accepted, in step 83 the external push notification service 23 provides a signed access token to the CP 3 which then proceeds with the remote programming process similar to the method shown in FIG. 5.

The token (MFA token) provided by the external push notification service 23 to the CP 3 is a signed JWT token which is also referred to as the RP session token or access token. The CP 3 provides this token to the RMS 1 in every RP transaction during the RP session. The token is valid for the duration of the current RP session, subsequent RP sessions require a new token which means having to go through the authentication sequence described above again.

In the following steps, the components of the system execute connectivity steps. For that, the following messages/information are utilized by the system and/or the method:

- Follow-up ID (a unique ID created for each follow-up session. Used for process control and auditing)
- The above-mentioned multifactor authentication token (MFA, i.e. the token of the RP session determined by 2-factor authentication).
- RpStartSession message: an entity requesting the start of a remote programming sequence and contains information to specify the target patient. This is used when the HCP selects a patient on the CUI for the remote session. RMS's remote-programming service triggers the associated PR 5 with a push notification as explained above. The PR 5 may start a replication, in case there are a lot of un-replicated data to catch up with.
- RpCpRequest message: containing the therapy program parameters
- RpPrRequest message: containing encrypted programming commands
- RpRmsStatus updates CP 3 with programming progress; captures the status of RMS's processing of the RP request with various timestamps, etc. This message contains, for example, time of RpCpRequest received, time of RpCpRequest signed by CKMS, time of RpPrRequest generated, time of push notification to PR sent, other state and error info
- RpCpStatus. The RpRmsStatus and RpPrStatus entities are used to communicate status at each hop. Each entity may contain tasks that each hop is responsible for performing, errors/status values, completion of tasks denoted by a timestamp.

The remote programming method further makes use of a "Time to Live" calculation (TTL) in its control process. As indicated above, TTL is a value in an Internet Protocol (IP) packet that tells a network router whether or not the packet has been in the network too long and should be discarded. This TTL is an absolute time in UTC. TTL is based on PR's 5 time to account for time synch mismatches between CP 3 and PR 5. TTL is calculated using current PR time acquired at session start and elapsed time since RMS data base synchronization and timeout interval. When PR receives RpPrRequest entity, it takes the TTL value and starts a timer. Expiration of TTL is communicated by setting the respective value in the RpPrStatus entity.

Figure 7:
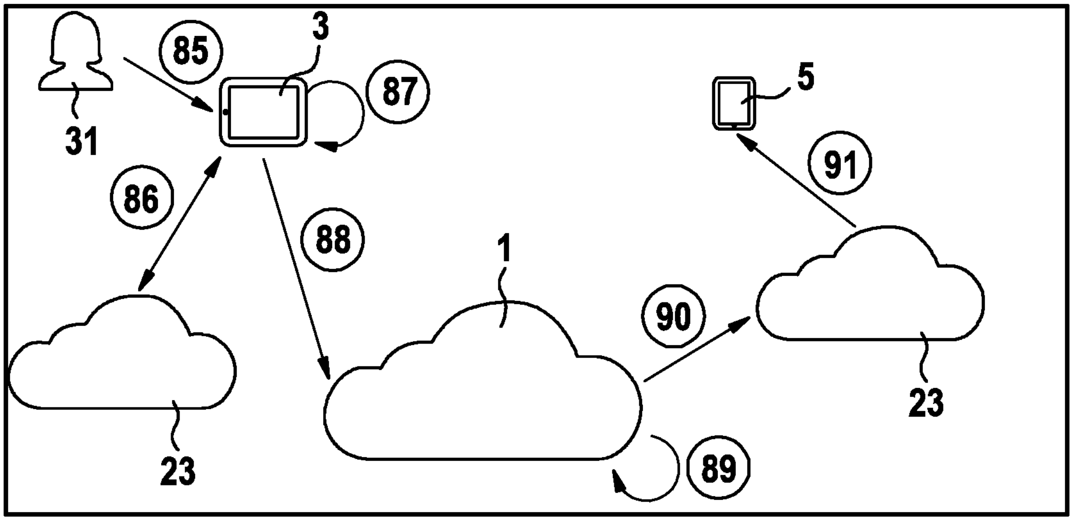
FIG. 7 depicts a flow diagram of initiating an RP session (CP to PR)

With regard to FIG. 7 further steps during initiation of an RP session are explained. This flow diagram shows that the PRs 5 are not configured to continuously poll the RMS 1 for changes as that would result in unnecessary overhead on both the PR 5 and the RMS 1. Instead, the RMS interfaces with the external push notification service 23 to send a notification to the target PR 5. For example, at the beginning of a remote programming session the target PR 5 receives a push notification. This notification serves as a trigger to the PR 5 to poll the RMS 1 (i.e. its Couchbase server 21) at a faster rate. The notification does not contain detailed information such as any identifying or secret data.

For example, the following steps may be executed for remote programming (i.e., remote follow-up). At first, the HCP selects a patient to program in step 85. The HCP navigates to the remote patient management page on the CUI found on the CP 3 and selects a patient from a filterable list of opted-in patients who the HCP is authorized to follow-up with. Such list is shown, for example, in FIG. 25. Then, the 2-factor authentication is provided as indicated with regard to FIGS. 5 and 6 above (step 86). At the same time, the CP 3 creates an entity requesting the start of an RP session (step 87), i.e. the CP 3 sends a RpStartSession command to the RMS. This means that an uplink is created from the CP 3 to PR 5. The CP 3 then waits for successful authentication, and for the PR 5 to respond with an object of the medical device 7 of the patient via RMS 1. Then, the RpStartSession is synchronized with the RMS 1 (step 88). After that, the RMS 1 identifies the target PR 5 which corresponds to the selected patient (step 89), e.g. using Google firebase. Then, a push notification request is sent to the external push notification service 23 (step 90), which contacts the PR 5 corresponding to the selected patient and the PR 5 receives the push notification and is thereby triggered to replicate with the RMS 1 at a faster rate (step 91).

Figure 9:
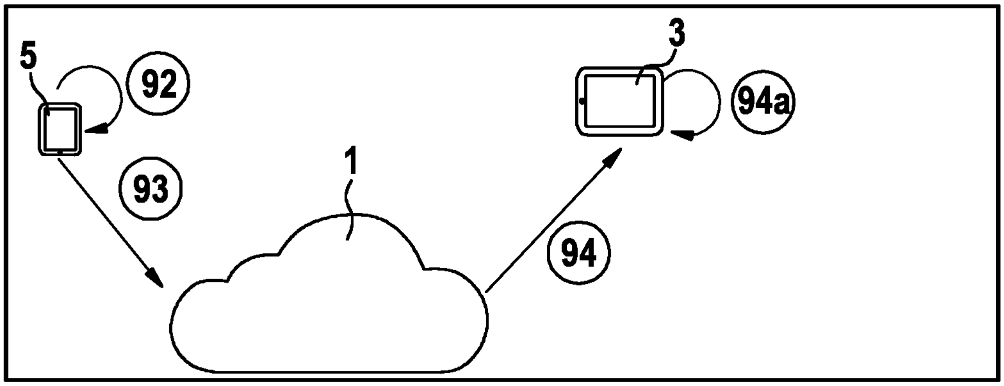
FIG. 9 shows a flow diagram of RP session, namely PR to CP response.

As a response, which is depicted in FIG. 9, the PR 5 synchronizes with the RMS 1 (step 93) after the current PR time and medical device connection state was placed into a response entity (step 92). For example, the current battery state, therapy data such as stimulation state, and/or MRI mode state, and any medical device errors or other data of the PR database will be sent from the PR 5 to the RMS 1. Similarly, the CP 3 synchronizes with the RMS 1 (step 94), wherein the above-mentioned data are further transmitted to the CP 3. Additionally, the CP 3 quotes data from relevant entities to start the remote programming session (step 94 a). Updates to this information will be delivered on a change in any of these items. If the CP user (e.g. HCP) has not begun editing a program, the PR will also update the CP via RMS 1 with any changes to the active program, program strength, or program start strength. Relevant status information will be logged using the normal logging mechanisms. If the response of the PR 5 is received within a pre-defined time (e.g. 30 seconds) of the CP 3 sending the RpStartSession command, and the response indicates that PR is connected to the medical device and has the expected follow-up ID, the CP enters the standard programming page in remote programming mode. Otherwise, CP displays an appropriate message and stays in the remote patient management page.

Figure 8:
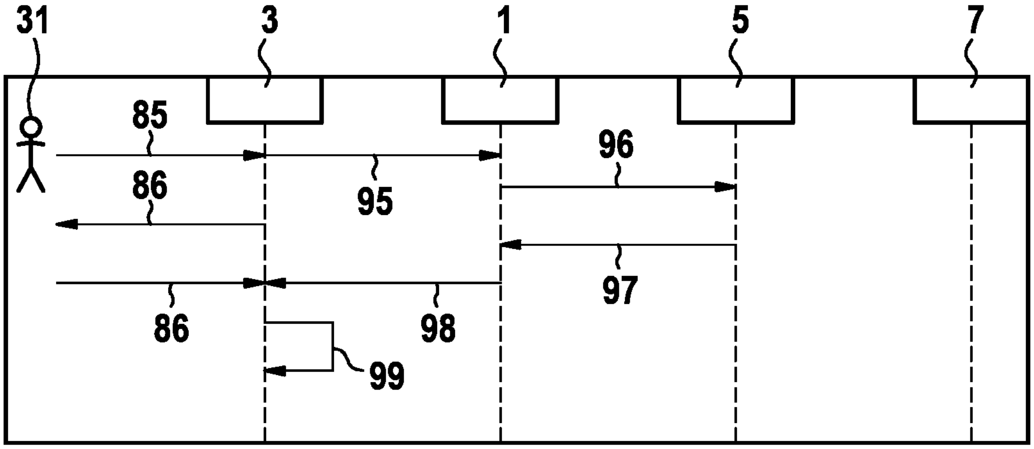
FIG. 8 shows a sequence diagram of initiating an RP session (CP to PR)
Figure 25:
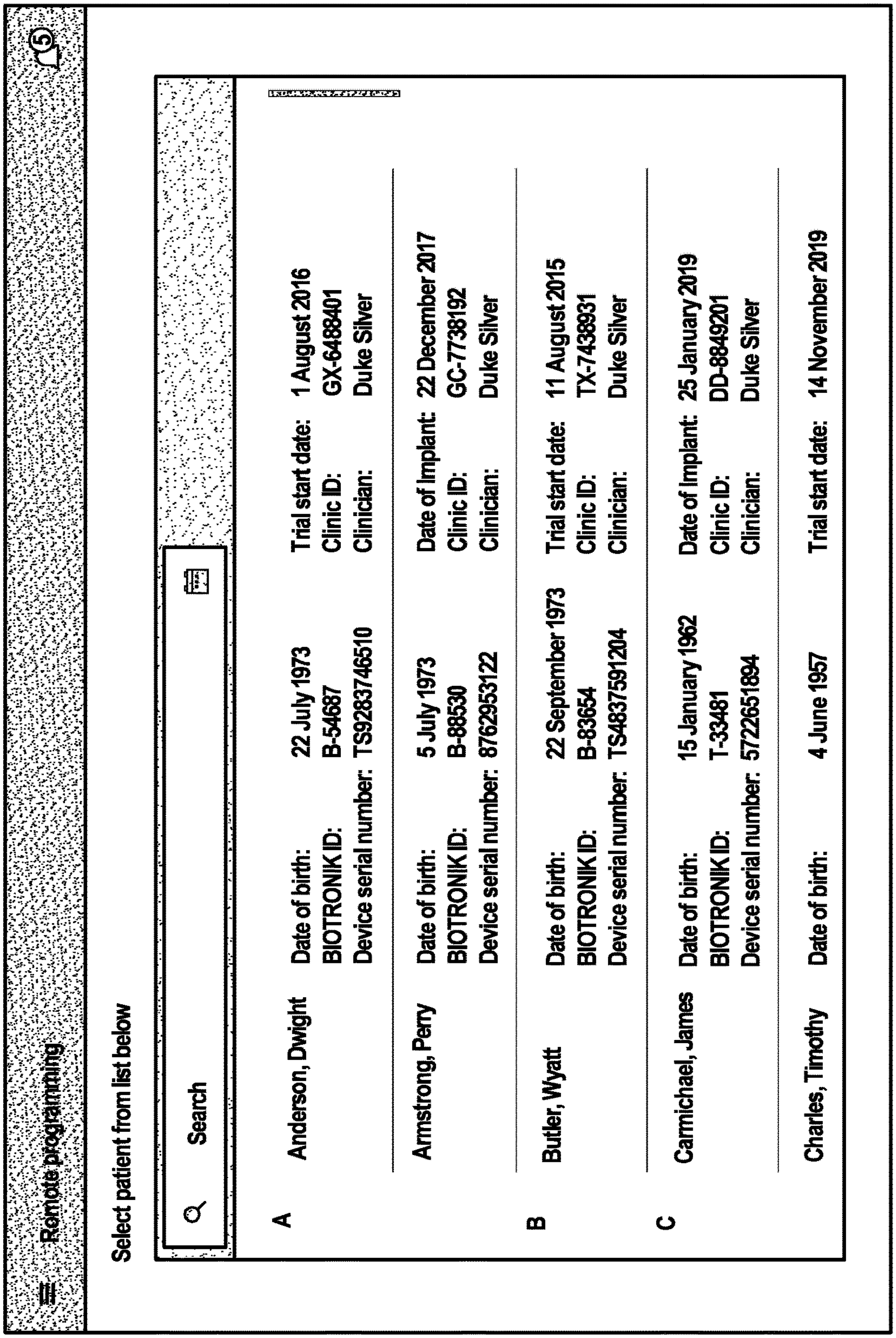
FIG. 25 shows an example of a CP screen during RP (patient selection)

FIG. 8 shows the start of the remote programming session as a sequence diagram which is explained in the following. As indicated above the HCP 31 first selects a patient who needs to receive a program update of his/her medical device 7 (step 85). An example for the screen were selecting a particular patient is shown in FIG. 25. The 2-factor identification illustrated above is provided by the steps 86. Then, a start session command sent from the CP 3 to the RMS 1 (step 95). In the next step 96 the RMS 1 sends a start session notification to the PR 5. Triggered by this command the PR 5 responds by sending information received from the medical device 7 previously (step 97). This information, for example, may comprise current battery state, stimulation state, MRI mode state, or any medical device errors. This information is further transmitted to the CP 3 in step 98. Further, CUI is updated in step 99 afterwards.

Figure 24:
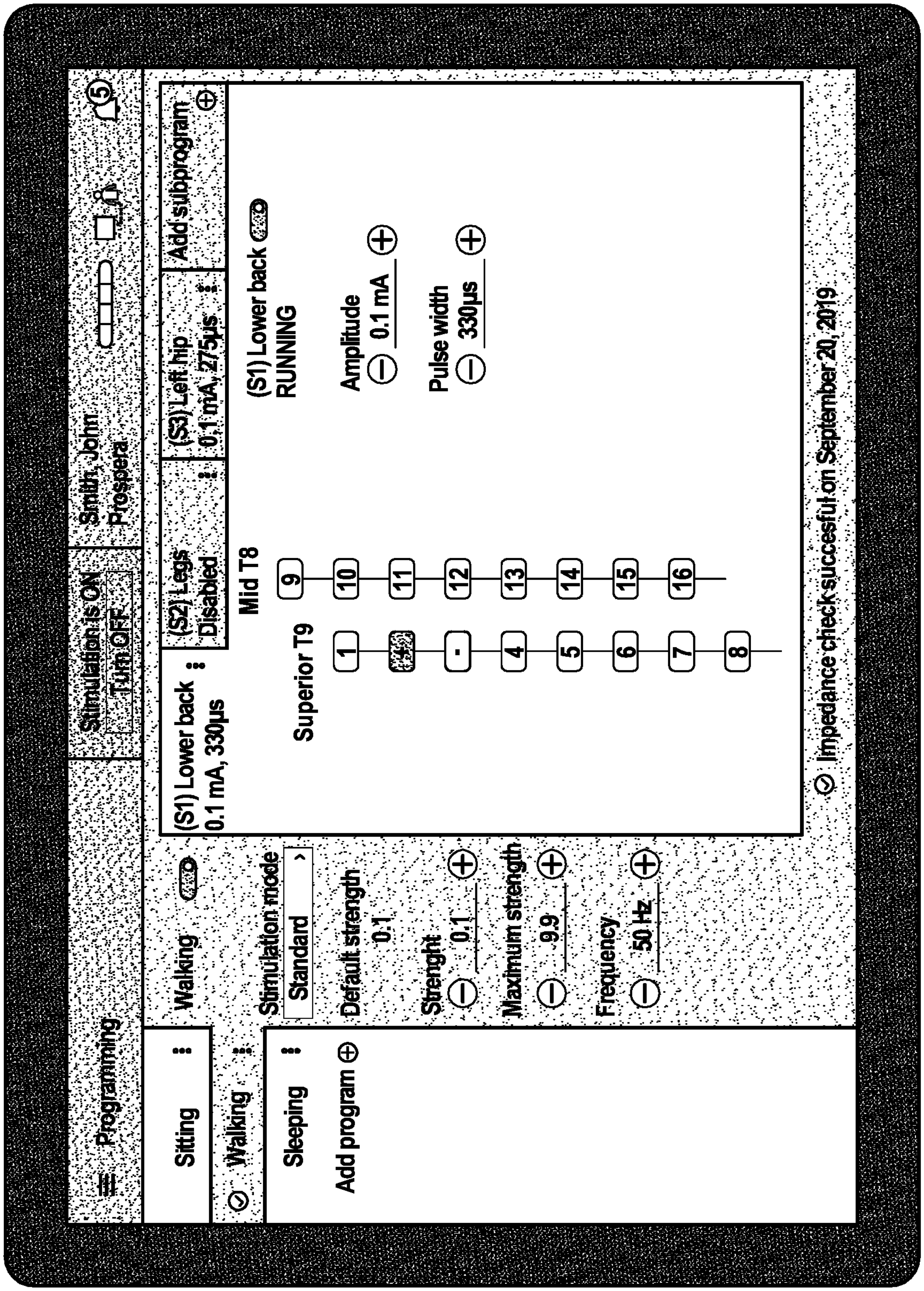
FIG. 24 shows an example of a CP screen during RP.
Figure 28:
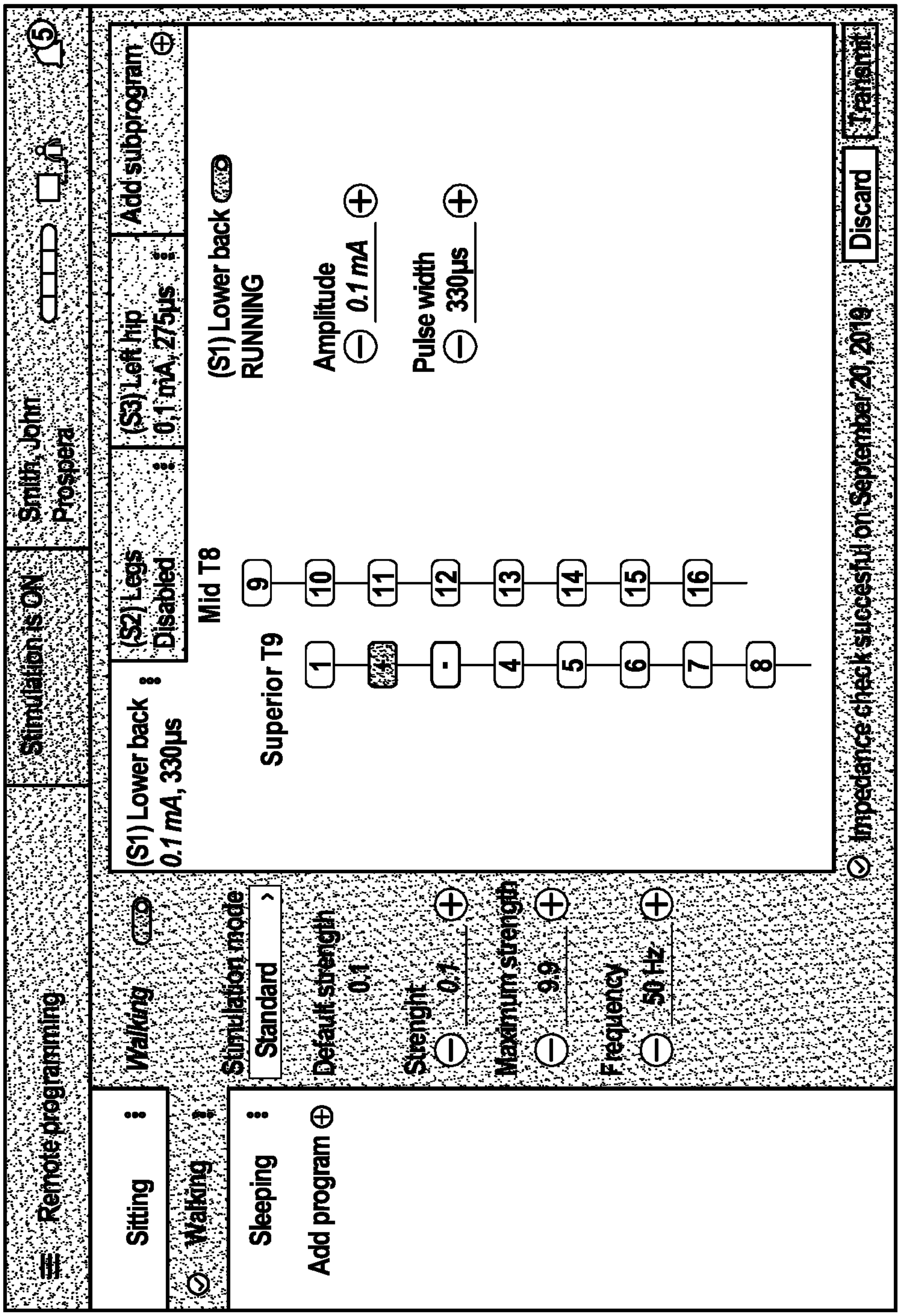
FIG. 28 shows an example of a CP screen during RP (program updated awaiting transmission)
Figure 29:
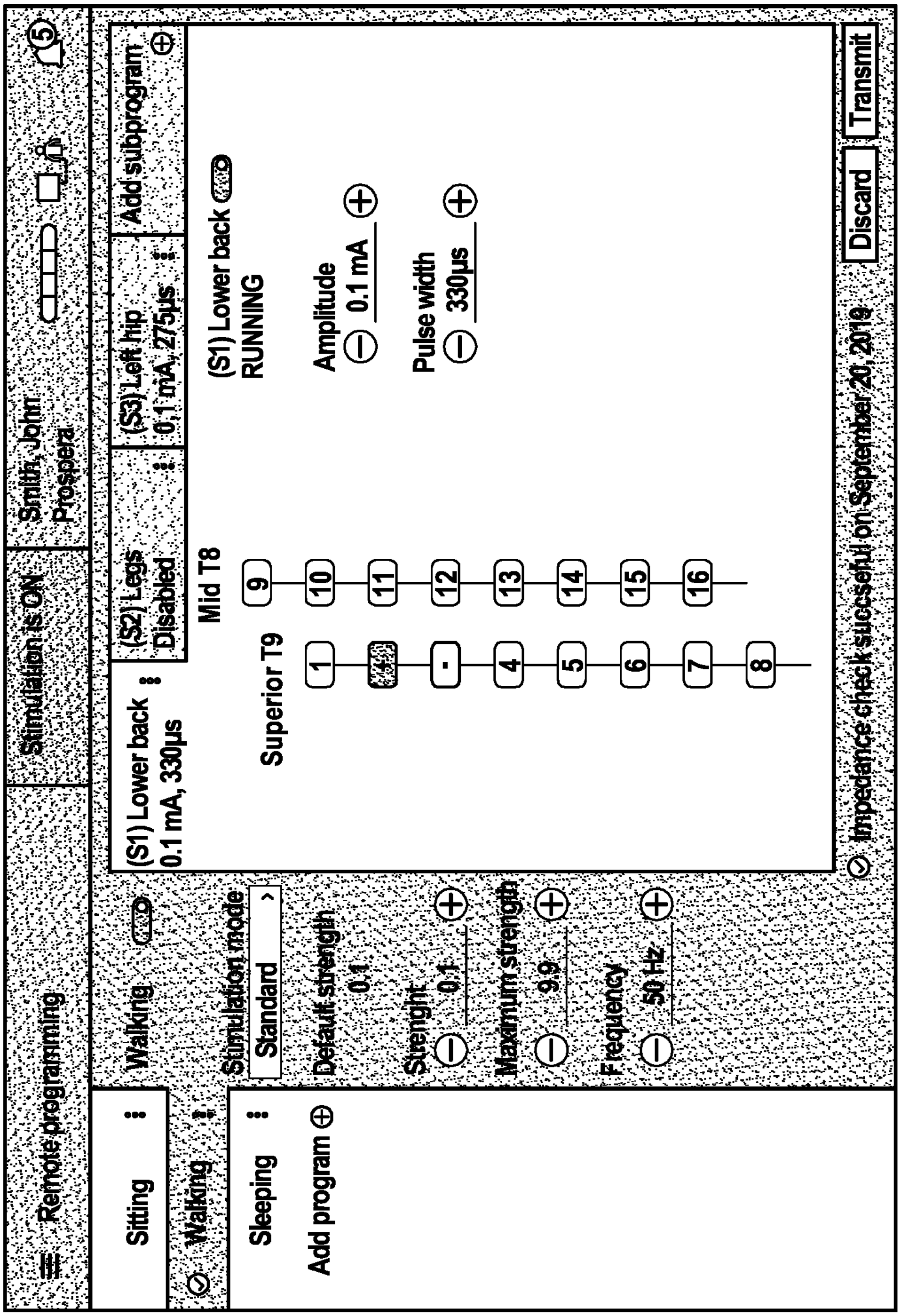
FIG. 29 shows an example of a CP screen during RP (reprogramming completed)

In the remote programming mode CP application stages parameter changes provided by the HCP 31 to a single therapy program using the programming CUI. Remote programming differs from face-to-face in that instead of transmitting changes immediately pending changes will be highlighted to indicate to the HCP 31 the changes that will be made. This can be derived from FIGS. 24 and 28 which contain examples of a programming screens of a CP 3. Attempting to switch programs prompts the HCP as the CP user to discard his/her changes or stay on the current program. If the HCP has made all desired changes and taps the transmit button a 'transmission in progress' overlay may be displayed to prevent navigation or further program edits. This overlay may persist until programming completes will be HCP chooses to end the session.

Figure 10:
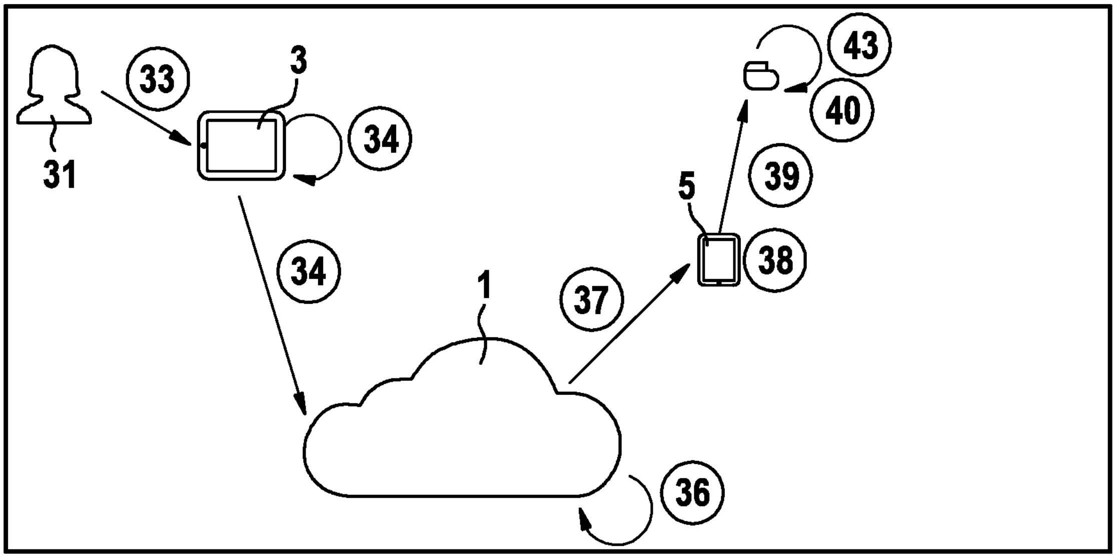
FIG. 10 depicts the RP session communication CP to PR to medical device.
Figure 11:
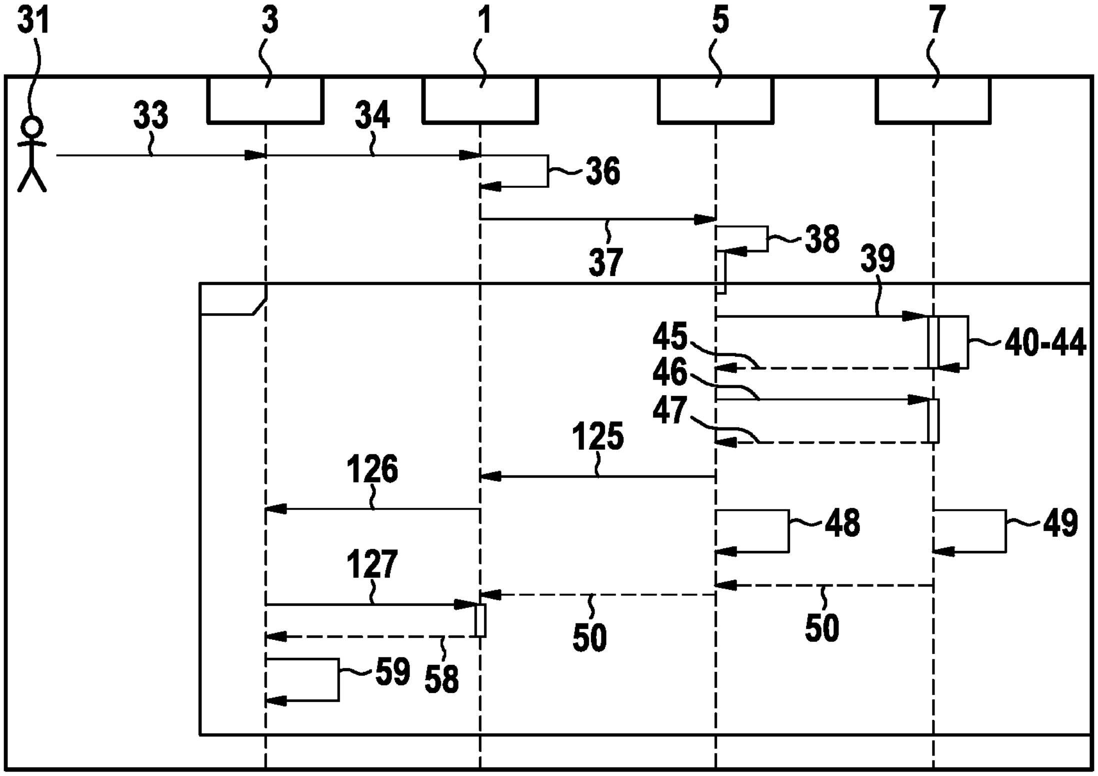
FIG. 11 shows a sequence diagram of RP with transmission acceptance.

The following steps of remote programming are visualized in FIGS. 10 and 11. Pressing the "Transmit" button starts the remote programming using the established communication chain CP-to-RMS-to-PR-to-medical device. The following steps describe uplink and downlink.

For the safety and comfort of the patient, all programs updated through remote programming will have their program strength set to a pre-defined minimum value. After successful programming, the patient may be required to adjust the medical device parameters, for example the strength and default strength to an appropriate level, using the standard PR 3 UI. If the remote programming session is still in progress, these changes will be reflected in the CP 3, as described above.

After pressing the transmit button (step 33, see FIG. 11), to perform the transmission, the CP 3 creates and sends an RpCpRequest entity, containing the therapy program parameters, to the RMS 1 (step 34). After program encryption (step 36), the RMS 1 then sends an RpPrRequest to the PR 5 containing encrypted programming commands (step 37) and creates an RpRmsStatus to update CP 3 with programming progress. The RMS 1 starts a Push Notification to the PR 5 so that the PR 5 may start a replication to get the RpPrRequest update as indicated above. The PR 5 does not parse this data. Upon receiving this request, if the TTL has not expired, the PR 5 asks the patient to accept or decline the program update (step 38).

Figure 12:
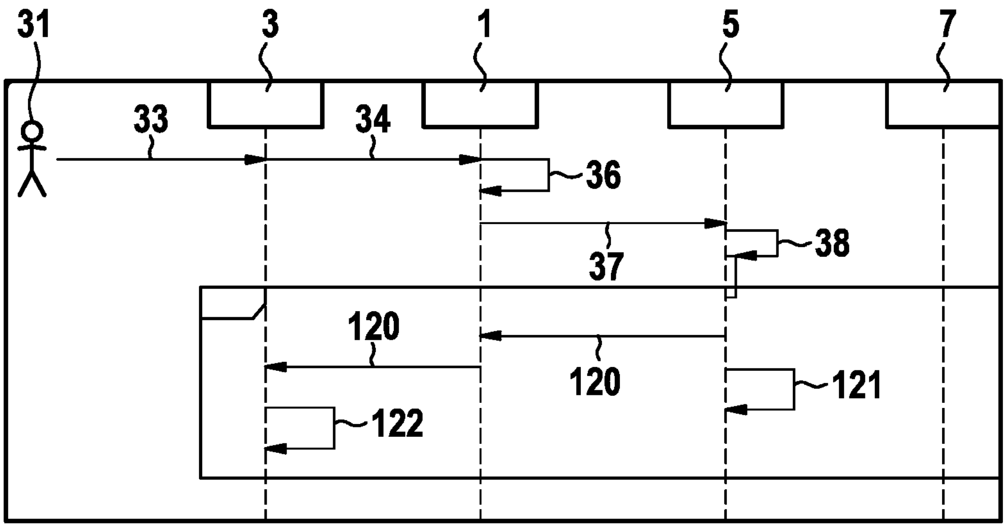
FIG. 12 shows a sequence diagram of RP with transmission rejection.

If the user rejects the update, which is shown in FIG. 12, the PR 3 will insert an RpPrStatus entity indicating the user rejected the update and a message is displayed to the PR 5 and CP 3 users via RMS 1 (steps 120). Accordingly, the UI of PR 3 and the CUI of CP 3 are updated (steps 121 and 122).

If the patient accepts the request in step 38 (see FIG. 11), the PR 3 sends the data to the medical device 7 using, for example, Bluetooth (step 39). The further steps 40 to 44 have already been explained with regards to FIG. 3. Upon completion the PR 5 will resynchronize with the medical device 7 (steps 46 and 47) and sends an RpPrStatus to the RMS 1 to indicate the result of the programming operation (step 125). If the follow-up ID or revision has changed, programming is considered to be successful, otherwise programming is determined to have failed. On successful programming, the CP 3 then receives an updated Follow-up entity from the RMS 1 which is loaded to continue the session (step 126). The following steps 58 and 59 have already been explained in connection with FIG. 3. If programming does not succeed, the CP 3 continues the session as it was prior to the "Transmit" button being pressed. The HCP uses the side menu end session option to end the session once all desired edits have been transmitted.

Figure 13:
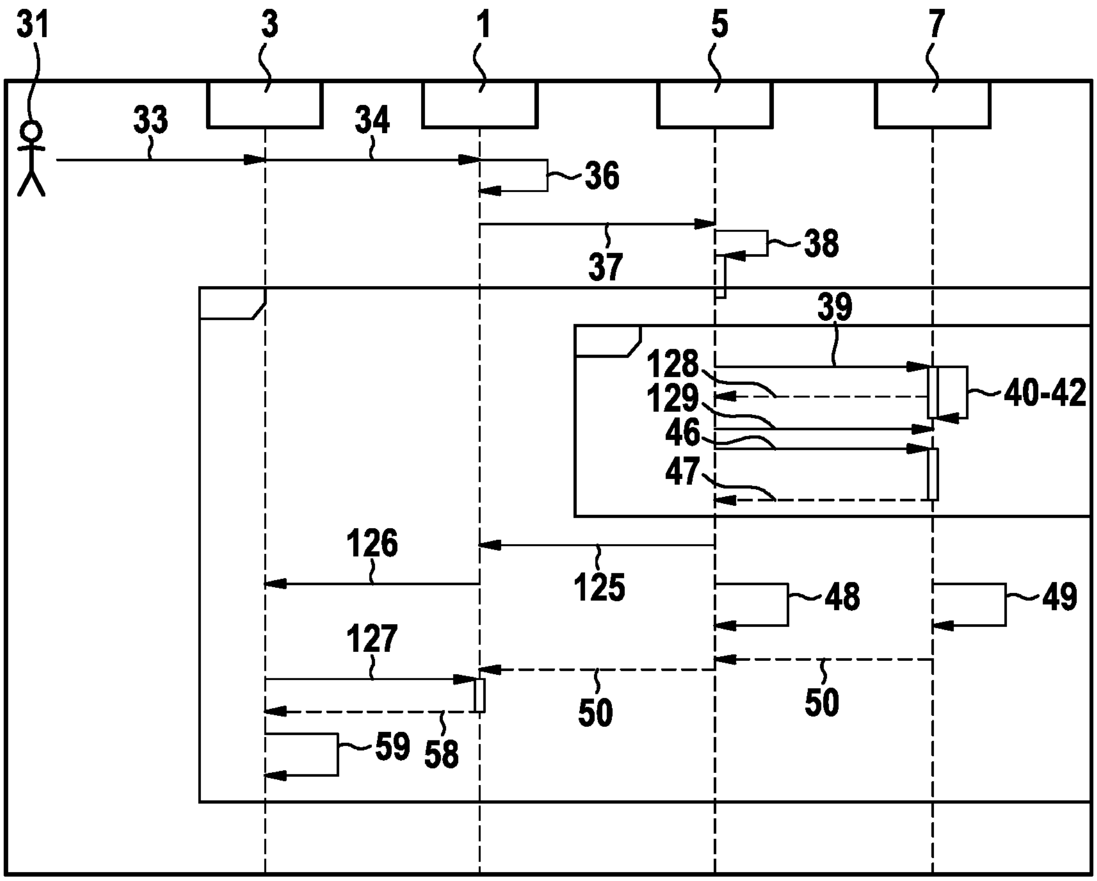
FIG. 13 shows a sequence diagram of RP transmission with connection loss.

During remote programming, it is possible for the PR 3 to lose connection to the medical device 7 which is depicted in FIG. 13 in step 128. In this case the PR will wait until a connection has been re-established (see step 129 in FIG. 13) and then resynchronize with the medical device 7. If after the completed resynchronization the follow-up ID or revision has changed, this will indicate successful programming. If the follow-up ID or revision has not changed the PR will retry the programming operation.

Figure 14:
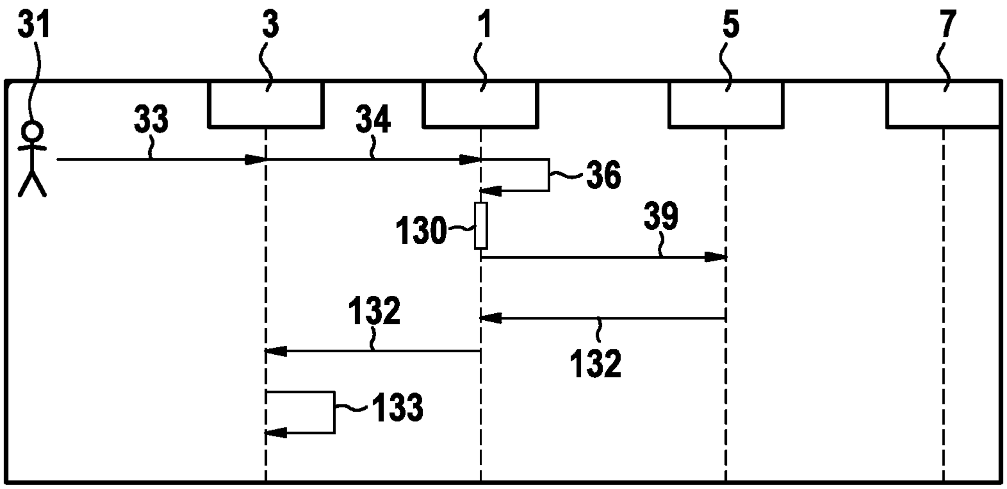
FIG. 14 depicts a sequence diagram of time to live (TTL) expiry before receipt.
Figure 15:
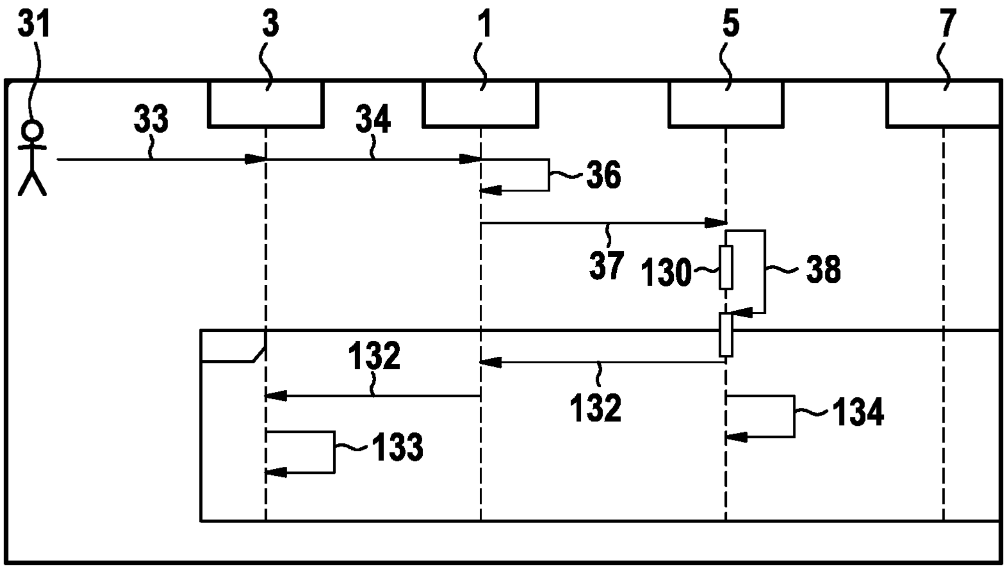
FIG. 15 depicts a sequence diagram of time to live (TTL) expiry before acceptance.
Figure 16:
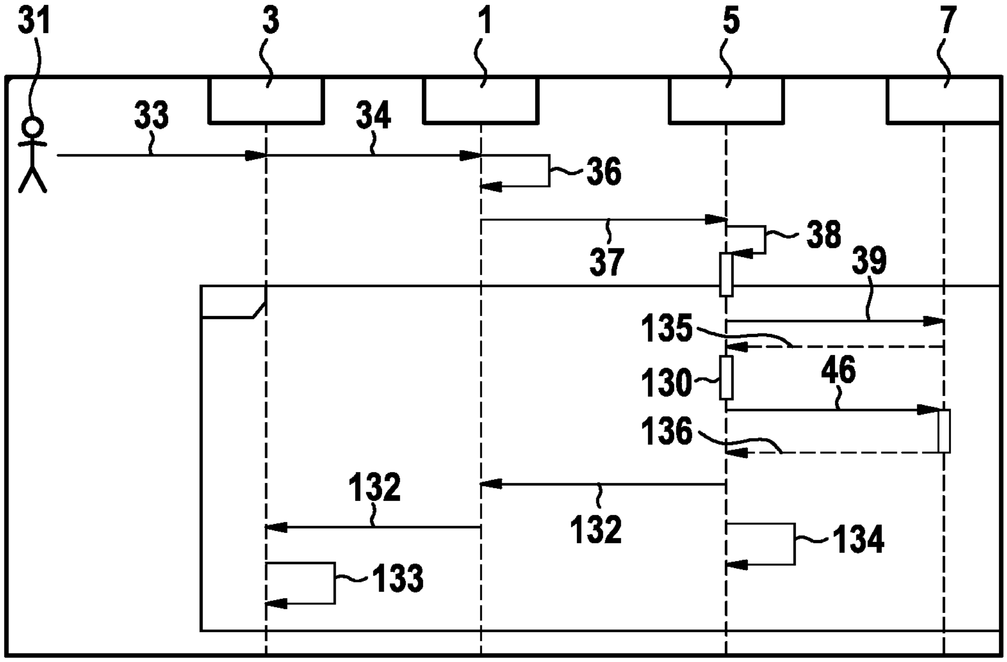
FIG. 16 depicts a sequence diagram of time to live (TTL) expiry during communication loss.

As indicated above, programming transmissions include a Time to Live (or TTL). If the instructions take longer to be transmitted to the medical device 7 than this pre-defined time, which is shown in FIG. 14 to 16 the programming operation is cancelled. There are three possible TTL scenarios.

In the first scenario shown in FIG. 14, the programming request takes longer to be received by the PR 5 than the TTL. I.e., the TTL expires (see step 130 in FIG. 14) prior the programming request is sent to PR 5 (step 39). In this case, no messages are displayed to the patient at the PR 5 and the PR 5 will send an RpPrStatus indicating the request was cancelled (step 132) which is transmitted via RMS 1 to CP 3, and CP 3 will display an appropriate message to the HCP 31 (CUI update 133).

In the second scenario, shown in FIG. 15, the PR 5 receives the request, but the patient does not accept the request within the TTL (i.e. TTL expiration 130 during prompting of the patient (step 38). This case operates the same as the first case, but an appropriate message is displayed to the patient at the PR 5 (see UI update in step 134 in FIG. 15).

The third case occurs when the PR 5 loses communication (step 135) to the medical device 7 during programming. In this case, which is shown in FIG. 16, once the PR 5 has reconnected with the medical device 7 the PR 5 will check for successful programming using the interrogation step 46. If it turned out that programming has not succeeded (step 136) and the TTL has expired (step 130), the PR 5 will send an RpPrStatus indicating the request was cancelled to CP 3 via RMS 1 (steps 132), and appropriate messages will be displayed to the PR user (patient) and the HCP 31 after CUI and UI update (steps 133, 134).

If, during remote programming, the CP 3 receives a RP 5 or medical device 7 update, or other entity, which indicates the follow-up ID or revision has changed to an unexpected value, the CP 3 will immediately notify the HCP and end the session. This scenario could occur if multiple CP's attempt to conduct remote programming sessions with the same PR 5 at the same time.

Some information needed for remote programming changes very frequently and thus the system does not/may not rely on the standard home monitoring process to transfer this information. For the purposes of RP 5, it needs to be up-to-date at the beginning of the remote programming session but it also needs to be continually updated after the remote programming session so that the CP 3 may see the patient amplitudes change in real time.

The PR therefore performs the following:

PR maintains the PatientDevice entity in its local database which among other things contains:

PatientNonPii DocID

ApplicationSpecific as a string—This is used for communicating information directly between a CP and PR.

"Fuel Gauge" Status (i.e. state of battery charge) (displayed on the CP)

MRI Mode or Not (i.e. enabled or not) (displayed on the CP)

Status of Master switch (displayed on the CP)

Status of Magnet mode (displayed on the CP)

Current Active Therapy (displayed on the CP)

Start Strength and Strength for all programs and sub-programs (merged with data transmitted by HM)

Connected or not connected state with the implant (displayed on the CP and checked)

Entity Revision of the follow-up entity from the implant (Checked for compatibility)

LIM (Lead Impedance Measurement) Enabled (used for calculation rules)

RemoteProgrammingState (Available, DataOutOfSyncWithImplant, SessionInProgress)

RpStartSessionID—null, if no RP session since last PR app launch current time on the PR's operating system clock PR autonomously synchronizes this state with the NSC on specific triggers:

start of RP session when PR app launches when BLE connection status changes when PR associates with a patient & implant when network connectivity is restored after being offline when the user taps 'Setting/Advanced/Refresh' always pushes on new data generated on the reception of a home monitoring message from an implant. (data)

On any change to a parameter relevant to Remote Programming

The system components are specified (e.g. memory, processing capability, transmission speed, etc.) such that they are capable of performing within the boundary requirements of the connectivity use case of the particular embodiment. For example, in the RP embodiment, the components must deliver at least the following system throughput requirements for input.

| Inputs | | | |
|---|---|---|---|
| LTE | Download | 22.69 | Mbps |
| (from PR's perspective) | | 2836.25 | KBps |
| (PR's speeds based on Speedtest's United States "2017 | Upload | 8.51 | Mbps |
| Mobile Report" (based on Q1-Q2 2017 data) | | 1063.75 | KBps |
| http://www.speedtest.net/reports/united-states/#mobile) | | | |
| BLE | Download | 344 | Kbps |
| (from medical device's perspective) | | 43 | KBps |
| The data rate is based on the assumption of 20 ms | Upload | 344 | Kbps |
| Connection Interval CI, the data payload of 215 bytes | | 43 | KBps |
| (MTU size of 251 bytes-36 bytes of App Protocol | | | |
| Overhead), and 4 data packets per CI (in the case of | | | |
| Android). | | | |
| r = (I_MTU bytes * n_packets)/t_CI s | | | |
| RP Msg Processing Time | CP | 1 | s |
| | PR | 1 | s |
| | RMS | 15 | s |
| | External Push notification System | 2 | s |
| | TD* | 1 | s |
| medical device BLE Message Processing Latency | | 1 | s |
| RP CMD Payload Size | | 3 | KB |
| Assuming this is the size of a single program (blob + implant data) | | | |
| RP CMD Document Size (Payload + 50% Overhead) | | 4.5 | KB |
| medical device Interrogation Data Size | | 36 | KB |
| Assuming PR interrogates all 12 programs after it receives an RP Success msg. | | | |
| RS RESP Document Size (payload + 50% Overhead) | | 54 | KB |
| *- Time it takes for TD to decrypt msg (in Mesquite), rule check program, installprogram, activateprogram, and send alert to PR. | | | |

| Hop to Hop Time | | |
|---|---|---|
| RP CMD from CP to RMS | 1.00 | s |
| CP time to encrypt data + time to push data, for example, via Couchbase (ignores Couchbase comm layer activity and takes simple approach of data rate of data size). | | |

-continued

| | | |
|---|---|---|
| RP CMD RMS Processing<br>Couchbase (for example) process duration + decrypting data using CP key + encrypting data using medical device key + duration to send a push notification via external service | 15.00 | s |
| RP CMD from RMS to PR<br>The time it takes for PR to receive push notification + time for PR to pull data from RMS (ignores Couchbase comm layer activity and takes the simple approach of transferring entire data packet based on transmission rate) + PR processing | 3.00 | s |
| RP CMD from PR to medical device<br>BLE transmission time + medical device processing time (receive msg decrypt msg, run rule check, install program) | 1.07 | s |
| PR Interrogate After RP Success Resp<br>Assuming PR reinterrogates all programs | 1.84 | s |
| RP RESP from PR to RMS<br>PR processing time + time to push data to RMS (assuming response sent back to NSC contains latest therapeutic data returned from medical device; ignores, e.g. Couchbase comm layer activity and takes the simple approach of transferring entire data packet based on transmission rate) | 1.05 | s |
| RP RESP RMS Processing<br>Couchbase (e.g.) process duration + duration to send a push notification via external service | 15.00 | s |
| RP RESP from RMS to CP<br>The time it takes for CP to receive push notification + time for CP to pull data from RMS (ignores Couchbase comm layer activity and takes the simple approach of transferring entire data packet based on transmission rate) + CP processing | 3.02 | s |

| Total Times | | |
|---|---|---|
| RP CMD from CP to PR | 19.01 | s |
| RP CMD PR to medical device + RP Install in TD (after patient ack) | 1.07 | s |
| PR Interrogation of medical device + RP RESP PR to RMS + RP RESP RMS to CP (after PR receives RP Success Resp) | 20.91 | s |
| Round Trip Time (ignoring patient ack time) | 40.98 | s |

The system further allows combining subjective (e.g. patient diary, patient surveys, HCP notes) and objective data (e.g. current patient status, patient trends and outcomes analysis, longitudinal pain data, activity-based tracking, medication use checking, statistics) into one viewable RMS database via multiple data reporters, for example, CP 3, PR 5, RMS 1 (for example NSC), Electronic Health Record system (EHR). Further, the RMS 1 provides a central service unit that serves as a central data repository of all of clinic's patients, as well as manages access rights and controls access to therapy device data according to user's log-in. The system may further comprise a web-based presentation layer, accessible from (1+N) different UI. The system may further provide HCP-accessible reporting which includes controlled access to database, configurable access rights within the database (i.e. to specific patient or groups of patients), accessible via multiple portals (CP, NSC UI, EHR UI, other). The HCP may view both current patient status as a real-time "snapshot" as well as via long-term data trends. The reporting may further comprise configurable report formats to allow customization to clinic or individual user's needs. The system further comprises a searchable patient and medical device database.

In the following the data organization/management in the RMS 1 is explained in detail also with regard to data security.

In connection with this, it turns out that an important feature of the system is that all data within the system may be organized such in the RMS 1 that they are accessible to employees of an external service provider (technician of the system, external HCP, statistics companies, for example, for patient's studies, companies offering medical devices which may receive further information on the behaviour of their product(s)) via certain tools/interfaces (e.g. a Data Warehouse (DWH), tools for the customer service, etc.), for example, for the purpose of post market surveillance of the used medical devices. The accessible data also include serial numbers, names, dates, etc. Accordingly, access rights are implemented to allow access to exactly that data that each employee needs in order to perform the task at hand. By offering all data via the interfaces of the RMS 1, the necessary access rights and related processes for being compliant with privacy laws may be defined independently of the design, development and maintenance of the RMS.

The concept mainly relies on two principles, namely, to categorize data as close to the origin as possible (i.e. CP, PR, RMS) into different data sets (see "Categories of Stored Data"), restrict access to data as close to the data user as possible (e.g. DWH and Customer Service Tools), based on clearance of use.

Medical, technical and connectivity data is collected by stimulators, PRs, CPs and the RMS frontend (the latter only collects data in future generations of the embodiment). Further data might be created during processing.

The data may be accessed by the sub-systems Data Warehouse (DWH) und Clinical Data Warehouse (CDW). If patients have given explicit consents for being included in studies, the DWH may import respective data from the RMS and offer them to service provider's internal users based on the user's access rights. The CDW may import pseudonymized and device identification data from those patients that are part in studies.

RMS may comprise customer support tools for the customer service. These tools may be used for 1st level troubleshooting, customer support and customer administration.

There may be an RMS frontend that allows/requires the HCP to directly interact with the RMS 1. In one embodiment external data reporters/consumers will allow for the secure exchange of data between external data reporters/consumers and the RMS.

The data in the RMS, the DWH and the CDW may be stored encrypted. Access rights are in place to ensure restricted access to the stored data. Physical access to the data bases is restricted to administrative staff. The RMS frontend end the RMS customer support tools do not store data themselves but may always request the data live from the RMS 1.

In one embodiment, each access point has a UI designed specifically for the functions performed.

The RMS 1 may also have a user interface which may realize a closed loop, real-time communication with the at least one medical device 7. For example, if the HCP wants to know the patient's data in preparation for follow-up consult or remote assistance call with the patient the HCP triggers a respective request (update data request) from the RMS 1. This request is then transmitted to the PR 5 which in turn relays the request to the medical device 7. The medical device queries current patient and device status and transmits the report to the RMS 1 via the PR 5. The report is received and processed (i.e. the message is converted to form usable by the RMS 1, scanned for alert conditions using internal algorithms and assigned to the correct clinic and patient) by the RMS 1. Then, the HCP is able to review the new report in advance of the in-person meeting. The interface may be used to display data received via regular routine to connect data automatically (daily, monthly, or the like) or on purpose (e.g. preparation for in-office visit, patient adjustment, . . . ). Further, the RMS 1 is configured to provide a current patient status 'snapshot' collected in near real-time showing all quantitative and subjective data stored for the patient. In addition, as indicated above, the RMS 1 provides online access to the PR and the medical device to collect real time data. The RMS 1 is further configured to provide the status of the patient's system and statistics collected over time (e.g. for an SCS device implanted lead integrity, present stimulation settings, the diagnostic trends related to pain or system use). In one embodiment, the user may have the ability to configure the display of the combined status such that different data trends are visible or invisible according to the user's preferences. The HCP's web interface of the RMS 1 may further provide an image of the patient, videos or audio files. Further, the interface may allow to query the database, for example for all patients or medical devices under control of the respective clinic.

Additionally, the RMS 1 may provide the feature of an electronic signature ability to allow the HCP and/or patient to electronically provide consent for future participation in remote follow up or scientific studies. Further, the RMS 1 may provide a capability for viewing population wide data for the clinic or for a medical device registry in order to look at overall outcomes or relationships of patient characteristics.

Figure 17:
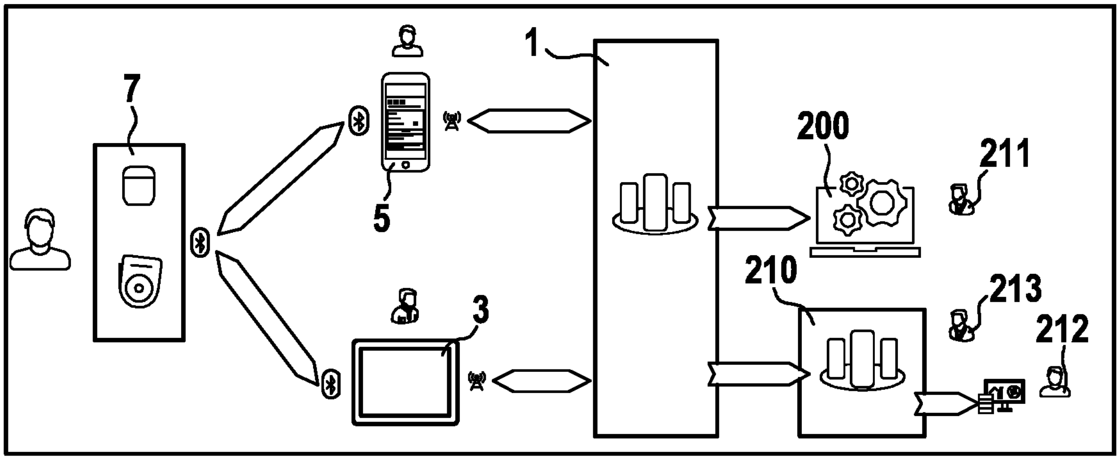
FIG. 17 shows an overview of another embodiment of an inventive system.
Figure 18:
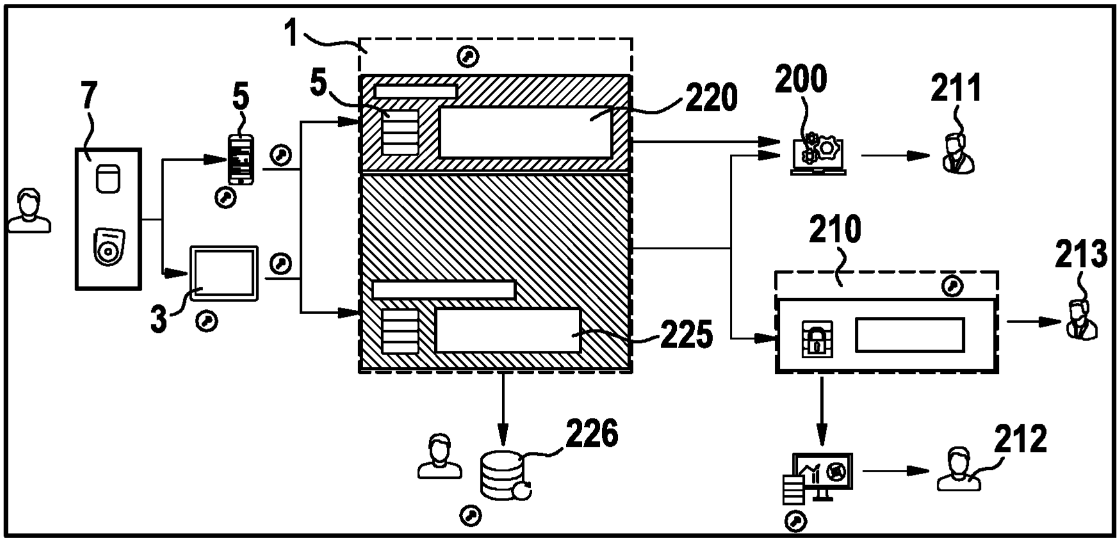
FIG. 18 depicts the embodiment of FIG. 17 in more detail regarding the system architecture.
Figure 19:
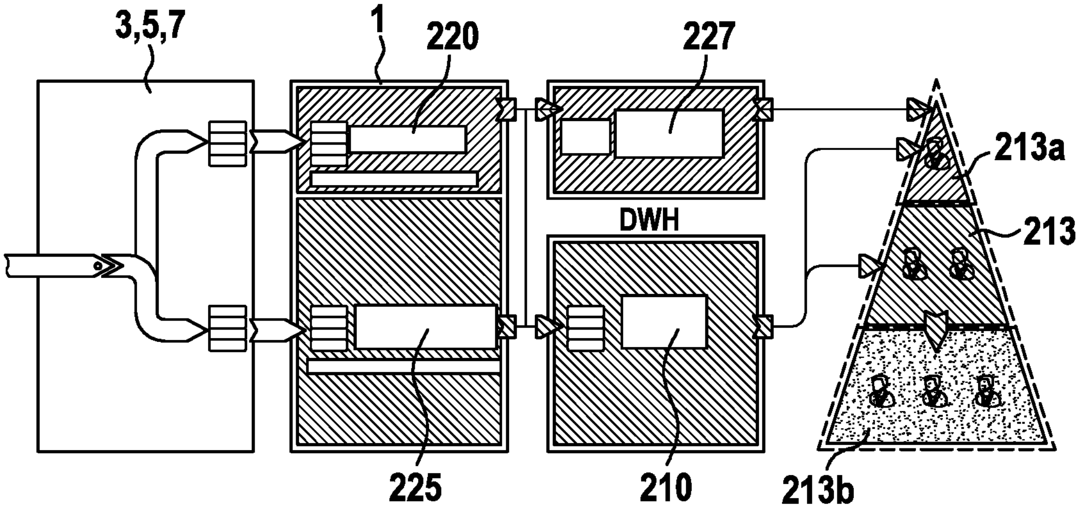
FIG. 19 shows a system data workflow and access diagram of another embodiment of the inventive system.
Figure 20:
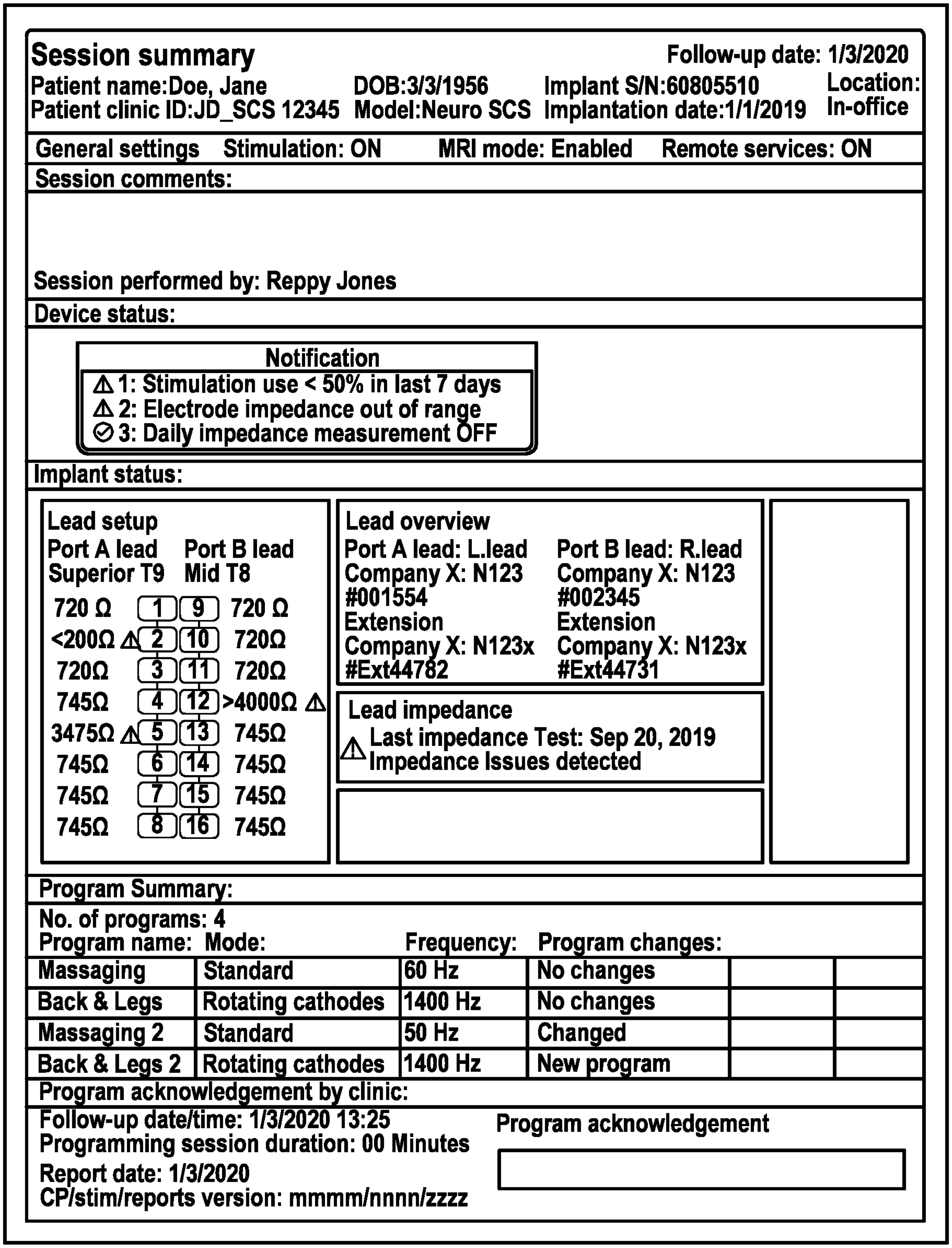
FIG. 20 shows an example of a session summary report.
Figure 21:
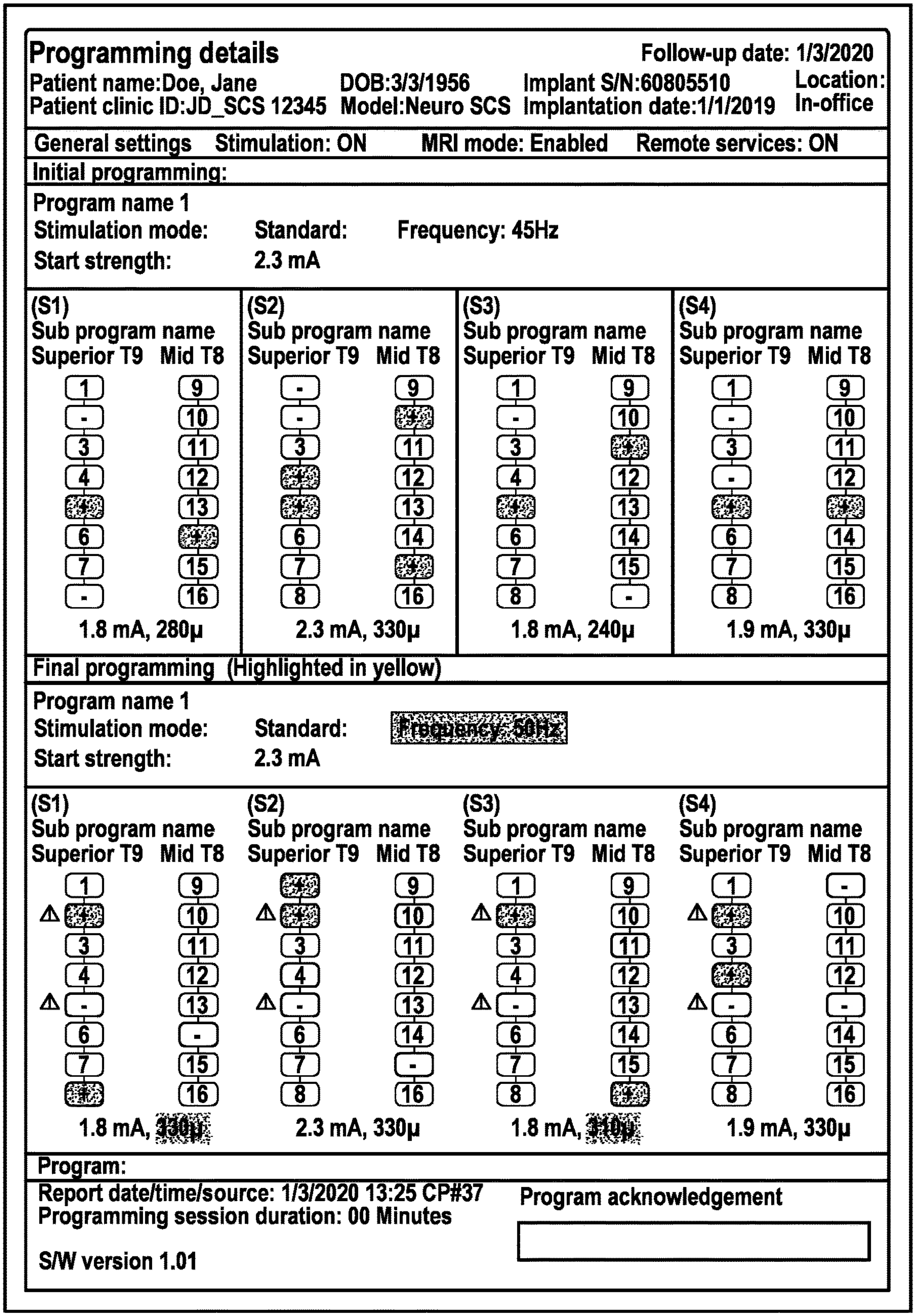
FIG. 21 shows an example of a programming details report.
Figure 22:
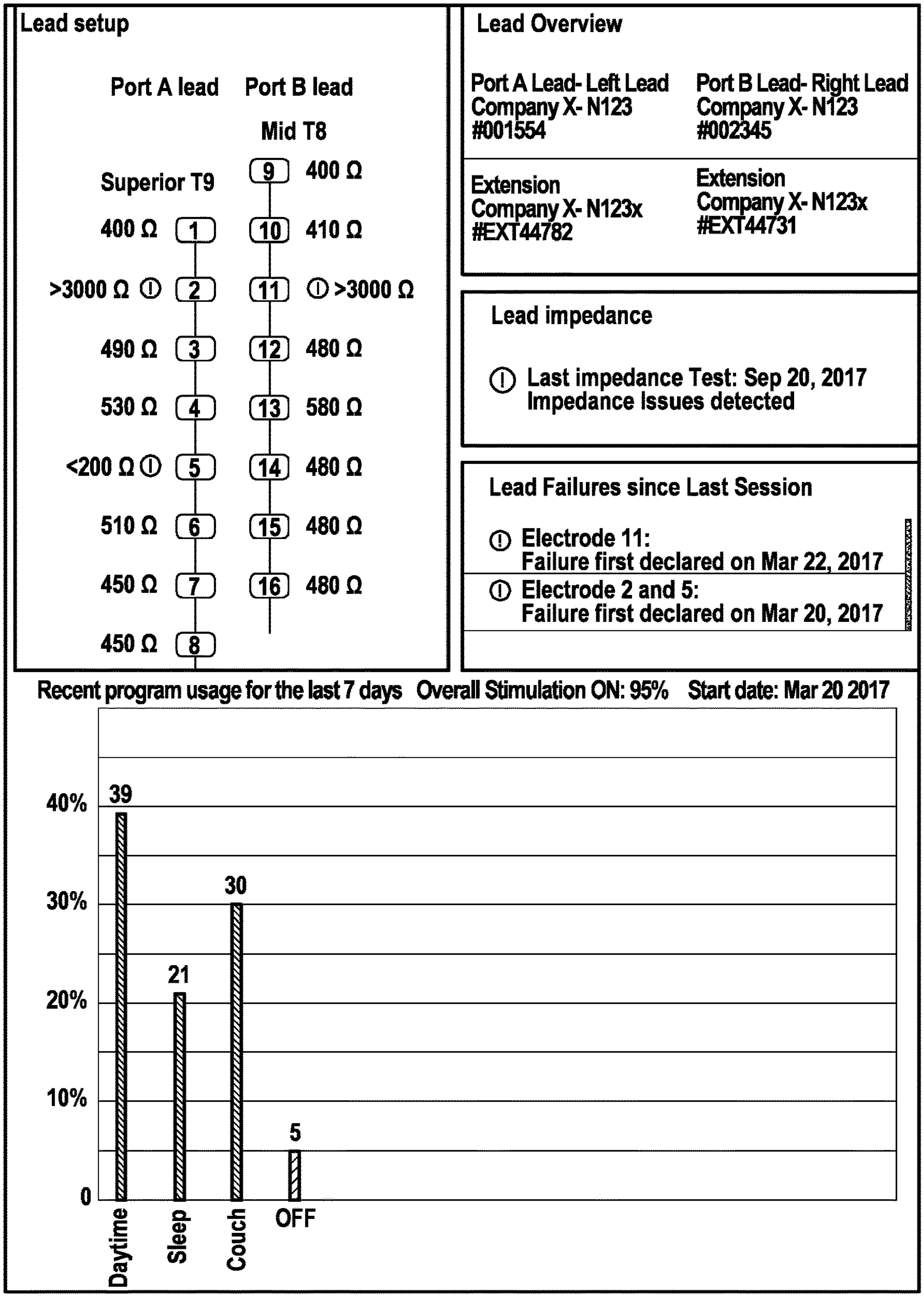
FIG. 22 shows an example of another session summary report (detail)
Figure 23:
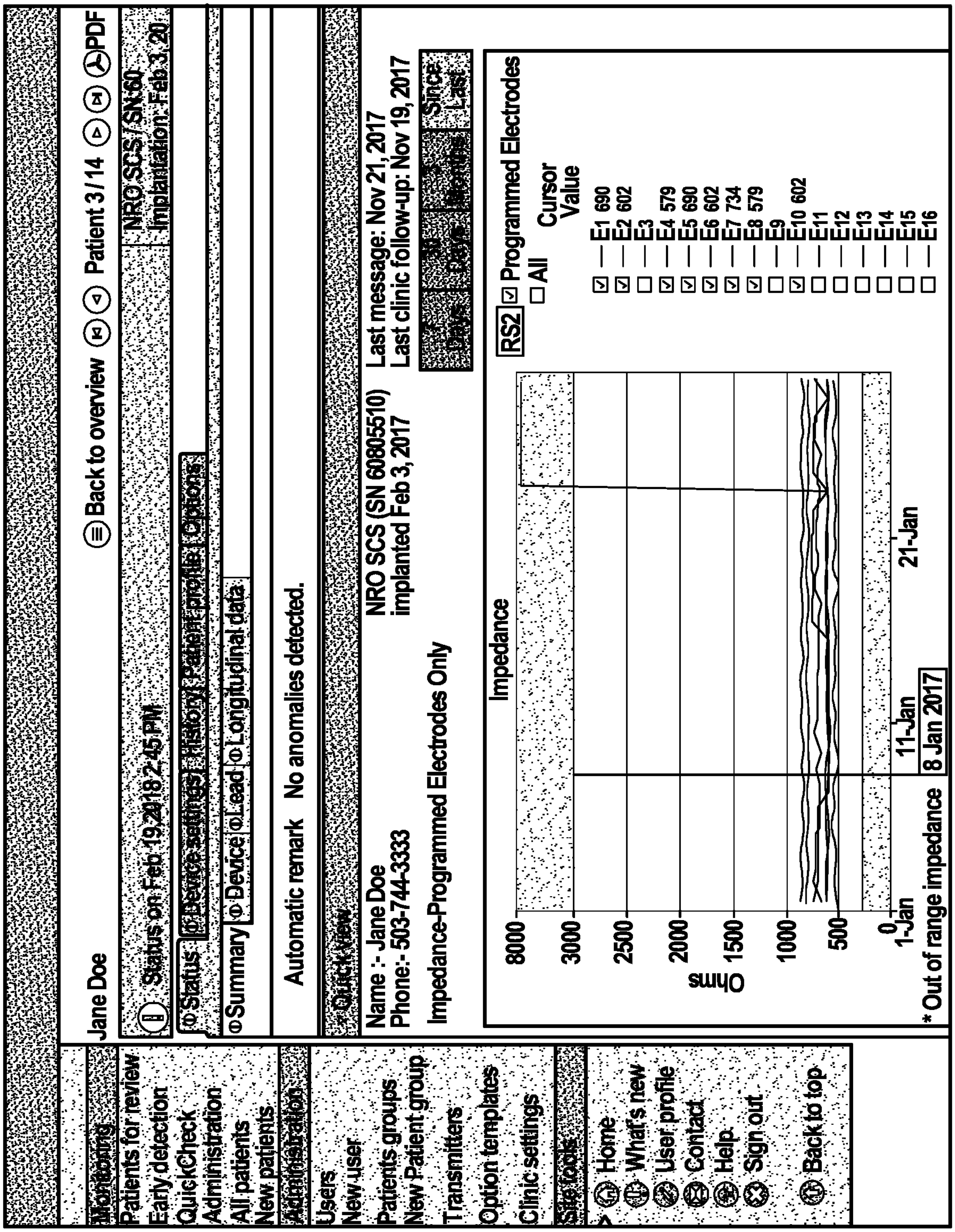
FIG. 23 shows an example of another session summary report.

FIGS. 17 to 19 show different embodiments of data and access organization of the system. FIG. 17 shows that the RMS 1 data are accessible for customer service tools 200 and for a data warehouse (DWH) 210. The customer service tools 200 are used to manage the RMS 1 and to fix problems on the hardware or software side by a technician 211 of the service provider. As indicated above, some of the data available in the RMS 1 may be provided to the DWH 210 for, for example, a post market surveillance or the respectively medical devices. These data may be available for study managers 212 or employees of the medical device manufacturer 213. The systems shown in FIGS. 17 and 18 further provide direct access of the CP 3 to the medical device 7. This may be helpful for in person follow-up the clinic.

FIGS. 18 and 19 show that the data stored in the RMS 1 may be associated with the different security level categories. One part of the data may be private or personal data 220 which need a higher level of protection than the pseudonymized data 225. The private or personal data 220 comprise, for example, names, addresses of patients, HCP or other users, patient record IDs, user IDs. The pseudonymized data 225 may comprise medical data, technical data, serial numbers, patient record IDs, user IDs. As one may derive from FIG. 18 the data warehouse 210 is allowed to access the pseudonymized data 225 only, whereas the customer service tools 200 need to have access to both, personal data 220 and pseudonymized data 225. Further, all data are stored in a backup storage 226.

In FIG. 19 it is shown that the employees of the medical device manufacturer may have different access rights. A first category of employees 213*a* may have access to personal data 220 via an interim storage 227 and pseudonymized data 225 via the DWH 210. The access to the interim storage 227 is highly restricted. After finishing the tasks using the data of the interim storage 227 these data are deleted. The tasks of this group of employees may comprise contacting users for regulatory reasons or due to discovered issues with specific medical devices or troubleshooting related to personal data 220. The second group and third group of employees 213, 213*b* have access to pseudonymized data 225, only. The second and second largest group of employees 213 may provide, for example, troubleshooting related to specific medical devices or monitoring of specific medical devices (post market surveillance). The third and largest group of employees 213*b* provides, for example, statistical monitoring of all medical devices assigned to the system, forward analysis or troubleshooting without the need to access identifiers.

Regardless of which UI the user may access patient data and/or the remote programming process through a common print application which used for generation of medical device report(s). These reports consolidate current and historical, as well as objective and subjective data, into the single report. The report uses multiple display types: text fields, tabular data and data graphs. Examples for such reports are shown in FIG. 20 to 23.

This process facilitates tracking or "visualization" of the reprogramming process, describing the status of the reprogramming as it occurs, up to an indication of the successful completion of the reprogramming and annotation of the patient record with the updated status, in real-time via continuous interrogation.

The invention further comprises the following embodiments:

A system (system embodiment 1) comprising at least one medical device, a remote monitoring server (RMS), at least one patient remote device (PR) and at least one health care professional (HCP) remote device (CP) wherein the system is configured such that for programming and/or interrogation of one chosen medical device, one CP establishes a communication session connecting the one CP via the RMS and the PR with the chosen medical device using the one CP by establishing a first bidirectional communication connection of the one CP and the RMS, triggering the RMS to establish a second bidirectional communication connection of the RMS and the PR corresponding to the chosen medical device and to establish a third bidirectional communication connection of the PR corresponding to the chosen medical device and the chosen medical device, wherein the system is configured to provide real-time remote programming and/or interrogation of the chosen medical device using the one CP via the RMS and the corresponding PR, and to maintain the first, second and third communication connections as continuous communication connections.

The above-mentioned system (system embodiment 1), wherein the RMS comprises a central data repository of data collected by the at least one CP, the at least one PR and/or the at least one medical device.

The system of any of the previous embodiments, i.e. system embodiment 1 and subsequent ones, wherein the RMS is configured to manage the at least one CP and the at least one PR.

The system of any of the previous embodiments, wherein the system is configured such that the continuous communication connections are maintained until a close signal is sent from the one CP to the chosen medical device via the RMS and the corresponding PR.

The system of any of the previous embodiments, wherein each of the at least one CP, the RMS and at least one PR comprise a data buffer for communication and/or the at least one medical device is configured to adjust its data sampling rate based upon the bandwidth of communication with the PR.

The system of any of the previous embodiments, wherein the RMS is configured to store and/or manage the authentication and/or encryption keys and/or certificates for the at least one CP, at least one PR, at least one medical device as well as for the at least one user of the system, for example, patient, HCP and/or technician.

The system of any of the previous embodiments, wherein the system comprises an authentication service which is configured to provide signed tokens to the at least one CP, wherein one signed token is valid for one particular remote programming session of the chosen medical device.

The system of any of the previous embodiments, wherein prior or during establishing a communication connection between the RMS and the corresponding PR the RMS is configured to send a push notification to the corresponding PR thereby triggering this PR to poll the RMS at a faster rate.

The system of any of the previous embodiments, wherein for remote programming of the chosen medical device the CP is configured to produce a single program containing the updates and/or changes of the medical device's parameters and to transmit the single program to the medical device via the RMS and the corresponding PR.

The system of last embodiment above, wherein the RMS is configured to encrypt the single program received from the CP, wherein the corresponding PR is configured to transmit the encrypted single program to the chosen medical device.

The system of any of the previous embodiments, wherein the RMS comprises a central data repository of data collected by the at least one CP, the at least one PR and/or the at least one medical device, and wherein the RMS is configured such that its central data repository comprises data having different security levels, wherein one example of data with a lower security level are pseudonymized data.

The system of any of the previous embodiments, wherein the RMS comprises a central data repository of data collected by the at least one CP, the at least one PR and/or the at least one medical device, and wherein the RMS is configured to be connected with a data warehouse and/or a clinical data warehouse, wherein the data warehouse and/or the clinical data warehouse are configured to import at least a part of the data stored in the central data repository.

The system of any of the previous embodiments, wherein the RMS and/or the data warehouse and/or the clinical data warehouse are configured such that its respective data are accessible to external users depending on the access rights of the respective user.

The system of any of the previous embodiments, wherein the CP is configured to establish the first, second and/or third bidirectional connection by a session request.

A method (method embodiment 1) for remote programming and/or interrogation of one chosen medical device of a system comprising at least one medical device, a remote monitoring server (RMS), at least one patient remote device (PR) and at least one health care professional (HCP) remote device (CP), wherein one CP establishes a communication session connecting the one CP via the RMS and the PR with the chosen medical device using the one CP by establishing a first bidirectional communication connection of the one CP and the RMS, triggering the RMS to establish a second bidirectional communication connection of the RMS and the PR corresponding to the chosen medical device and to establish a third bidirectional communication connection of the PR corresponding to the chosen medical device and the chosen medical device, wherein real-time remote programming and/or interrogation of the chosen medical device is provided using the one CP via the RMS and the corresponding PR, wherein the first, second and third communication connections are maintained as continuous communication connections.

The above-mentioned method (method embodiment 1), wherein the RMS comprises a central data repository (e.g. 21 in FIG. 2) of data collected by the at least one CP, the at least one PR and the at least one medical device.

The method of any of the previous embodiments, i.e. method embodiment 1 and subsequent ones, wherein the RMS manages the at least one CP and the at least one PR.

The method of any of the previous embodiments, wherein the continuous communication connections are maintained until a close signal is sent from the one CP to the chosen medical device via the RMS and the corresponding PR.

The method of any of the previous embodiments, wherein the each of at least one CP, the RMS and at least one PR comprise a data buffer for communication and/or the at least one medical device adjusts its data sampling rate based upon the bandwidth of communication with the PR.

The method of any of the previous embodiments, wherein authentication and/or encryption keys and/or certificates are stored and/or managed for the at least one CP, at least one PR, at least one medical device as well as for the at least one user of the system, for example, patient, HCP and/or technician.

The method of any of the previous embodiments, wherein the system comprises an authentication service which provides signed tokens to the at least one CP, wherein one signed token is valid for one particular remote programming session of the chosen medical device.

The method of any of the previous embodiments, wherein prior or during establishing a communication connection between the RMS and the corresponding PR the RMS sends a push notification to the corresponding PR thereby triggering this PR to poll the RMS at a faster rate.

The method of any of the previous embodiments, wherein for remote programming of the chosen medical device the CP produces a single program containing the updates and/or changes of the medical device's parameters and transmits the single program to the medical device via the RMS and the corresponding PR.

The method of last embodiment above, wherein the RMS encrypts the single program received from the CP and sends it to the corresponding PR, wherein the corresponding PR transmits the encrypted single program to the chosen medical device.

The method of any of the previous embodiments, wherein the RMS comprises a central data repository (e.g. 21 in FIG. 2) of data collected by the at least one CP, the at least one PR and the at least one medical device, and wherein the central data repository of the RMS comprises data having different security levels, wherein one example of data with a lower security level are pseudonymized data.

The method of any of the previous embodiments, wherein the RMS comprises a central data repository (e.g. 21 in FIG. 2) of data collected by the at least one CP, the at least one PR and the at least one medical device, and wherein the RMS is connected with a data warehouse and/or a clinical data warehouse, wherein the data warehouse and/or the clinical data warehouse import at least a part of the data stored in the central data repository.

The method of any of the previous embodiments, wherein the data of the RMS and/or of the data warehouse and/or of the clinical data warehouse are accessible to external users depending on the access rights of the respective user.

The method of any of the previous embodiments, wherein the first, second and/or third bidirectional connection is established by a session request.

A computer program product comprising instructions which, when executed by at least one processing unit, cause the at least one processing unit to perform the steps of the method according to any of the previous method embodiments (method embodiment 1 and subsequent ones).

Computer readable data carrier storing a computer program product according to last embodiment above.

The invention claimed is:

1. A method for establishing a communication connection between at least one health care professional remote device (CP) and at least one medical device, comprising the steps:

(a) establishing a first communication connection between the CP with a remote monitoring server (RMS);

(b) establishing a second communication connection between the RMS and a patient remote device (PR); and (c) establishing a third communication connection between the PR and the medical device, wherein:

(i) the CP is configured to optimize an internal device process such that the first communication connection can be maintained as continuous communication connection, and/or (ii) the PR is configured to optimize an internal device process such that the second and/or third communication connection can be maintained as continuous communication connection, wherein a remote programming session and/or interrogation session of the medical device is initiated if the communication connection between the CP and the medical device is successfully established, and wherein each of the first, second, and third communication connections are in series to thereby establish the communication connection between the CP and the medical device.

2. The method of claim 1, wherein the CP and/or PR is configured to optimize an internal device process by at least one of:

(i) reducing a number of internal device software applications and/or reducing an internal device access to software applications to those required for maintaining the first communication connection as continuous communication connection, (ii) reducing internal device data traffic to that required for maintaining the first communication connection as continuous communication connection, or (iii) reducing internal device communication applications to that required for maintaining the first communication connection as continuous communication connection.

3. The method of claim 1, wherein for establishing the second communication connection between the RMS and the PR, the RMS initiates delivery of a notification from an external messaging provider to the PR.

4. The method of claim 3, wherein the PR, upon receiving the notification, starts polling information from the RMS at a predetermined rate.

5. The method of claim 1, wherein the remote programming session and/or interrogation session is associated with at least one first session identifier.

6. The method of claim 5, wherein the first session identifier is discarded when the communication connection between the CP and the medical device is lost, and wherein a new session identifier is generated when the communication connection between the CP and the medical device is reconnected.

7. The method of claim 6, wherein, after reconnecting the communication connection between the CP and the medical device, a remote programming session and/or interrogation session is declared valid if the new session identifier is different from the first session identifier.

8. The method of claim 1, wherein in case of a connection loss of the third communication connection, the PR is configured to attempt a reconnection between the PR and the medical device.

9. The method of claim 1, wherein the PR automatically transmits data associated with the medical device to the RMS upon at least one trigger event.

10. The method of claim 9, wherein a trigger event comprises at least one of:

(i) initiation of a remote programming session and/or interrogation session of the medical device, (ii) activation of an internal device software of the PR for establishing the second or third communication connection, (iii) establishing or changing the third communication connection, (iv) reconnection of the communication connection between the CP and the medical device, (v) an information update is requested via the CP, or (vi) a change of an information relevant to the remote programming session and/or interrogation session of the medical device.

11. A non-transitory computer readable storage medium including a computer program product comprising instructions which, when executed by at least one processing unit, cause the at least one processing unit to perform the steps of the method according to claim 1.

12. A system comprising at least one medical device, a remote monitoring server (RMS), at least one patient remote device (PR), and at least one health care professional remote device (CP), wherein the system is configured such that for programming and/or interrogation of one chosen medical device, one CP establishes a communication session connecting the one CP via the RMS and the PR with the chosen medical device using the one CP by establishing a first bidirectional communication connection (14) of the one CP and the RMS, triggering the RMS to establish a second bidirectional communication connection of the RMS and the PR corresponding to the chosen medical device and to establish a third bidirectional communication connection of the PR corresponding to the chosen medical device and the chosen medical device, wherein the system is configured to provide real-time remote programming and/or interrogation of the chosen medical device using the one CP via the RMS and the corresponding PR, and to maintain the first, second and third communication connections as continuous communication connections, wherein the programming and/or interrogation of the at least one medical device is established by the first, second, and third bidirectional communication connection being in series with one another to thereby establish a direct line of communication between the one CP and the at least one medical device, wherein:

(i) the CP is configured to optimize an internal device process such that the first communication connection can be maintained as continuous communication connection, and/or (ii) the PR is configured to optimize an internal device process such that the second and/or third communication connection can be maintained as continuous communication connection.

13. The system according to claim 12, wherein the CP and/or PR is configured to optimize an internal device process by at least one of:

(i) reducing a number of internal device software applications and/or reducing an internal device access to software applications to those required for maintaining the first communication connection as continuous communication connection, (ii) reducing internal device data traffic to that required for maintaining the first communication connection as continuous communication connection, and (iii) reducing internal device communication applications to that required for maintaining the first communication connection as continuous communication connection.

14. The system of claim 12, wherein the RMS is configured to initiate delivery of a notification from an external messaging provider to the PR for establishing the second communication connection between the RMS and the PR.

15. A method for establishing a communication connection between at least one health care professional remote device (CP) and at least one medical device, comprising the steps:

(a) establishing a first communication connection between the CP with a remote monitoring server (RMS);

(b) establishing a second communication connection between the RMS and a patient remote device (PR); and (c) establishing a third communication connection between the PR and the medical device, wherein:

(i) the CP is configured to optimize an internal device process such that the first communication connection can be maintained as continuous communication connection, and (ii) the PR is configured to optimize an internal device process such that the second and/or third communication connection can be maintained as continuous communication connection, wherein the optimization of the internal device process includes disabling at least one program in each of the CP and the PR, wherein a remote programming session and/or interrogation session of the medical device is initiated if the communication connection between the CP and the medical device is successfully established, wherein the remote programming session and/or interrogation session is associated with at least one first session identifier, wherein for establishing the second communication connection between the RMS and the PR, the RMS initiates delivery of a notification from a third-party external messaging provider to the PR.

16. The method of claim 15, wherein the CP and/or PR is configured to optimize an internal device process by at least one of:

(i) reducing a number of internal device software applications and/or reducing an internal device access to software applications to those required for maintaining the first communication connection as continuous communication connection, (ii) reducing internal device data traffic to that required for maintaining the first communication connection as continuous communication connection, or (iii) reducing internal device communication applications to that required for maintaining the first communication connection as continuous communication connection.

17. The method of claim 15, wherein the PR, upon receiving the notification, starts polling information from the RMS at a predetermined rate.

18. The method of claim 15, wherein the disabling of the at least one program includes at least one of: disabling messaging apps on the CP and/or PR, or limiting access of the CP and/or PR to an app store to a reduced set of apps.

19. The method of claim 1, wherein the optimization by the CP and/or the PR is unrelated to battery power management.

20. The method of claim 15, wherein the first communication connection is maintained as continuous communication connection after the optimization by the CP, wherein the second communication connection is maintained as continuous communication connection after the optimization by the PR, and wherein the third communication connection is maintained as continuous communication connection after the optimization by the PR.

* * * * *